US010254161B2

(12) United States Patent
Lee et al.

(10) Patent No.: US 10,254,161 B2
(45) Date of Patent: Apr. 9, 2019

(54) OPTICAL WAVE GUIDE HAVING MULTIPLE INDEPENDENT OPTICAL PATH AND OPTICAL GAS SENSOR USING THAT

(71) Applicant: Korea National University of Transportation Industry-Academic Cooperation Foundation, Chungju-si, Chungcheongbuk-do (KR)

(72) Inventors: Seung Hwan Lee, Chungju-si (KR); Sung Ho Jang, Seoul (KR); Sang Ho Jung, Seongnam-si (KR)

(73) Assignee: Korea National University of Transportation Industry-Academic Cooperation Foundation, Chungju-si, Chungcheongbuk-Do (KR)

( * ) Notice: Subject to any disclaimer, the term of this patent is extended or adjusted under 35 U.S.C. 154(b) by 22 days.

(21) Appl. No.: 15/368,679

(22) Filed: Dec. 5, 2016

(65) Prior Publication Data

US 2017/0082488 A1    Mar. 23, 2017

Related U.S. Application Data

(62) Division of application No. 14/264,575, filed on Apr. 29, 2014, now abandoned.

(30) Foreign Application Priority Data

Feb. 3, 2014    (KR) ........................ 10-2014-0012013

(51) Int. Cl.
*G01J 1/42*    (2006.01)
*G01J 1/04*    (2006.01)
(Continued)

(52) U.S. Cl.
CPC ........... *G01J 1/4228* (2013.01); *G01J 1/0422* (2013.01); *G01J 3/021* (2013.01); *G01J 3/0216* (2013.01);
(Continued)

(58) Field of Classification Search
CPC ........ G01J 1/4228; G01J 1/0422; G01J 3/021; G01J 3/0216; G01J 3/42; G01N 21/3504;
(Continued)

(56) References Cited

U.S. PATENT DOCUMENTS 4,815,858 A * 3/1989 Snail ................... G01N 21/474
356/446
5,973,326 A * 10/1999 Parry ................... G01N 21/031
250/341.8
(Continued)

FOREIGN PATENT DOCUMENTS

KR        10-0694635 B1    3/2007
KR        10-0732708 B1    6/2007
(Continued)

*Primary Examiner* — John R Lee
(74) *Attorney, Agent, or Firm* — Hauptman Ham, LLP

(57) ABSTRACT

The present disclosure relates to an optical gas sensor including at least: an optical wave guide including a first elliptical mirror formed along at least part of a first 3-dimensional ellipsoid and having a first focal point and a second focal point, a second elliptical mirror formed along at least part of a second 3-dimensional ellipsoid and having the first focal point and a third focal point, and a third elliptical mirror formed along at least part of a third 3-dimensional ellipsoid and having the first focal point and a fourth focal point; one or more optical sensors installed at at least one of the first, second, third, and fourth focal points; and one or more light sources installed at at least one of the first, second, third, and fourth focal points where the one or more optical sensors are not installed.

7 Claims, 33 Drawing Sheets
(24 of 33 Drawing Sheet(s) Filed in Color)

(51) Int. Cl.
*G01N 21/3504* (2014.01)
*G02B 6/10* (2006.01)
*G02B 27/10* (2006.01)
*G01J 3/02* (2006.01)
*G01J 3/42* (2006.01)

(52) U.S. Cl.
CPC ............ *G01J 3/42* (2013.01); *G01N 21/3504* (2013.01); *G02B 6/10* (2013.01); *G02B 27/106* (2013.01); *G01N 2201/08* (2013.01); *G02B 2207/117* (2013.01)

(58) Field of Classification Search
CPC .... G01N 2201/08; G02B 6/10; G02B 27/106; G02B 2207/117
See application file for complete search history.

(56) References Cited

U.S. PATENT DOCUMENTS

| | | | | |
|---|---|---|---|---|
| 6,194,735 | B1* | 2/2001 | Martin | G01N 21/031 250/222.2 |
| 7,609,375 | B2* | 10/2009 | Park | G01N 21/031 250/339.13 |
| 8,193,502 | B2* | 6/2012 | Hodgkinson | G01N 21/0303 250/339.12 |
| 8,796,629 | B2* | 8/2014 | Martin | G01N 21/031 250/343 |
| 9,239,291 | B2* | 1/2016 | Sakamoto | G01N 21/3504 |
| 9,448,158 | B2* | 9/2016 | Knutson | G01N 21/6458 |
| 9,777,375 | B2* | 10/2017 | Ikeda | F27B 17/0025 |
| 2002/0118362 | A1* | 8/2002 | Saccomanno | G01N 15/1456 356/246 |
| 2006/0226367 | A1* | 10/2006 | Hopkins | G01N 21/031 250/343 |
| 2007/0085023 | A1* | 4/2007 | Debroche | G01N 15/1456 250/458.1 |
| 2014/0338591 | A1* | 11/2014 | Ikeda | F27B 17/0025 117/220 |
| 2015/0219491 | A1* | 8/2015 | Lee | G02B 6/10 250/227.14 |
| 2017/0082488 | A1* | 3/2017 | Lee | G02B 6/10 |
| 2017/0167913 | A1* | 6/2017 | Berthoud | G01J 1/0422 |

FOREIGN PATENT DOCUMENTS

| | | |
|---|---|---|
| KR | 10-2009-0091433 A | 8/2009 |
| KR | 10-2009-0121810 A | 11/2009 |
| KR | 10-2011-0011307 A | 2/2011 |
| KR | 10-2011-0059006 A | 6/2011 |
| KR | 10-1088360 B1 | 12/2011 |
| KR | 10-2013-0058781 A | 6/2013 |
| KR | 10-2013-0082482 A | 7/2013 |

\* cited by examiner

30°

50°

70°

90°

OPTICAL WAVE GUIDE HAVING MULTIPLE INDEPENDENT OPTICAL PATH AND OPTICAL GAS SENSOR USING THAT

CROSS REFERENCE TO RELATED APPLICATION

The present application is a divisional application of U.S. patent application Ser. No. 14/264,575 filed on Apr. 29, 2014, which claims the benefit of priority from Korean Patent Application No. 10-2014-0012013, filed on Feb. 3, 2014, in Korean Intellectual Property Office (KIPO). The disclosures of the above-listed applications are hereby incorporated by reference herein in their entirety.

DESCRIPTION

Field of Invention

The present invention relates to optical wave guide having multiple independent optical path and optical gas sensor using that, and more particularly providing an optical wave guide having multiple independent optical path and Optical Gas Sensor using that that may condense light irradiating from a light source without a separate condenser within a range of tens~hundreds μm from the center of an optical sensor part, and reducing loss of amount of light by realizing a structure with a long optical path and also a structure minimizing reflection of light and at the same time skillfully condensing light on an optical sensor part, and able to actively deal with secular changes of light source.

BACKGROUND OF INVENTION

Generally, optical wave guides are manufactured so that optical path lengths in the process when light emitted from a light source arrives at an optical sensor part are made long and at the same time efficiency of transmittance of light in respect to optical sensor part is maximized. Optical wave guides are core configurations of optical gas sensors, and a number of publications were made public before the application of the present invention.

Korean Patent No. 10-0694635, 10-0732708, 10-1088360 and Korean Patent Laid-open Publication 2013-82482 are basically realized in an elliptical structure, and Korean Patent Laid-open Publication No. 2009-121810 and Korean Patent Laid-open Publication No. 2011-59006 comprises a condenser in front of a sensor part. Meanwhile, Korean Patent Laid-open Publication No. 2009-91433 and Korean Patent Laid-open Publication No. 2011-11307 has a reference sensor or a reference light source for improvement of reliability of sensor characteristics.

FIG. 1 is a drawing showing the characteristics of Korean Patent No. 10-0694635. First focal point and second focal point are formed in an elliptical dome shaped reflector (10). A light source (11) is positioned at the first focal point of an elliptical dome shaped reflector (10), and an optical sensor (12) is positioned at the second focal point of an elliptical dome shaped reflector (10). A flat surface reflector (13) is formed as a concaved flat mirror surface to condense infrared rays reflecting from an elliptical dome shaped reflector (10) after emitting from a light source (11). A light sensor (12) is installed horizontally on an elliptical dome shaped reflector (10) to receive all of the infrared rays reflecting from a flat surface reflector (13) and light directly irradiating from a light source (11).

Korean Patent No. 10-0694635 adopts a structure that uses only half of an elliptical dome shaped reflector (10) and directing light reflecting from the other half to an optical sensor (12) through a reflector. This structure is a structure using only less than half of light flux of an irradiating light, in the case of light irradiating and reflecting in lower flat surfaces, there are disadvantages of difficulty of adequately irradiating to an optical sensor (12) when passing though a filter attached to an optical sensor (12) due to refraction.

FIG. 2 is a drawing illustrating a main example provided by Korean Patent No. 10-1088360. According to FIG. 2, first elliptical mirror (111) and second elliptical mirror (112) of an optical wave guide (110) is formed along a portion of an entire trajectory of each first ellipse (111a) and second ellipse (112a) sharing a first focal point (111b, 112b).

A light source (120) is installed at first focal point (111b, 112b) shared by a first ellipse (111a) and a second ellipse (112a). A first light detecting window (131) and a second light detecting window (132) transmit light reflected from a first elliptical mirror (111a) and a second elliptical mirror (112a). A photo sensor part (130) detects light transmitting through a first light detecting window (131) and a second light detecting window (132). This structure has advantages of being easily manufactured in small sized structures, and is a structure able to condense without additional lens. But, the optical wave guide (110) of Korean Patent No. 10-1088360 structurally inherits disadvantages of condensing maximum of only ¼ of light from two light detecting windows.

The structure proposed in Korean Patent Laid-open Publication 2013-82482 is a structure gathering light emitted by a light source placed on a first focal point F1 of a first parabolic mirror (151) by a light detector placed on second focal point F2 of second parabolic mirror (152). According to FIG. 3, it shows advantages of measuring from two or more optical sensors are possible according to the shape and placement methods of the two parabolic mirrors (151, 152). But the structure using only two parabolic mirrors (151, 152), as proposed by J. S. Park and S. H. Yi in Sensors and Materials (thesis in year 2011), is a structure having disadvantages of not being able to effectively use light because condensing pattern shows a shape other than a round shape.

The structure proposed in Korean Patent Laid-open Publication 2009-121810, as illustrated in FIG. 4, has advantages of being able to improve optical sensing by comprising a lens (162) condensing light irradiating from a light source (161) to an optical sensor part (162). But, there are disadvantages of optical path being relatively short, and increased manufacturing costs due to installation of additional lens.

The structure proposed in Korean Patent Laid-open Publication 2011-59006, as illustrated in FIG. 5, has advantages of being able to improve light intensity by adopting a lens in front of an infrared sensor (174), but has disadvantages of increase in cost due to use of additional components and amount light arriving at an optical sensor part becoming relatively small by adopting a reflector (172) to increase optical path.

The structure proposed in Korean Patent Laid-open Publication 2011-11307, as illustrated in FIG. 6, has a reference sensor or a reference light source for improving sensor reliability. But has structural disadvantages of having lower optical sensor part (230) output compared to that of a structure with a lens because there is no special structure to condense incident infrared rays in the front-end of a photo sensor part (230).

The structure proposed in Korean Patent Laid-open Publication 2009-91433, as illustrated in FIG. 7, may periodically compensate the output of an infrared sensor (350) using a reference light source (310) and a main light source (320), in other words, multiple light sources. Also, it has a structure that may increase sensitivity of an infrared sensor (350) by making the optical path longer through multiple reflectors (361, 362, 363, 364). But, it may show disadvantages of being difficult to use for gas measurements for long wavelength ranges (>6 μm) as pattern of light arriving at an infrared sensor (350) incidents in parallel.

FIG. 8 is a drawing illustrating the relationship between blackbody radiation and light intensity. When using an infrared lamp, equation for light intensity ($B_T$) of each wavelength range irradiating from a filament (a light source with a temperature of about 4000K) inside a vacuum glass sphere is expressed as equation (1).

$$B_\lambda(T) = \frac{2hc^2}{\lambda^5} \frac{1}{e^{\frac{hc}{\lambda k_B T}} - 1} \quad \text{equation (1)}$$

T: absolute temperature, $k_B$: Boltzmann constant, h: Planck constant, c: velocity of light As expressed in FIG. 8 and equation (1), optical energy irradiating for gas detection is inversely proportional to approximately fifth power of a wavelength. When wavelength is long, output of an optical sensor part may be predicted to be marginal as intensity of incident light is small. Therefore, a structure for effectively condensing incident light to an optical sensor part is inevitable for improving sensor output.

Also, Beer-Lambert Law, which is applied broadly for infrared gas sensor manufacturing and applications, may be expressed as equation (2).

$$I = I_0 \cdot (-\alpha x l) \quad \text{equation (2)}$$

Io: an initial light intensity, α: absorption coefficient for specific gas, x: density of gas, l: optical path.

To improve output of an infrared gas sensor, as equation (3) proposed by J. S. Park and S. H. Yi in Sensors and Materials (thesis in year 2011), it may be observed that an incident light arriving at an optical sensor part emulating a condensed shape rather than an initial optical pattern is effective.

$$V = \zeta \left(\frac{r_i}{r_d}\right)^2 \cdot (-\alpha x l) \quad \text{equation (3)}$$

ζ: proportional constant, $r_i$: radius of initial optical pattern, $r_d$: radius of optical pattern at a sensor.

Looking into items that should be considered for manufacturing optical gas sensors as expressed in formula (1), (2), (3), 1) since light intensity of a light source decreases from secular change of its own filament, it should be appropriately compensated by sensing secular change according to time,
2) and when gas with long wavelengths is to be measured, it should be a high performance sensor able to sufficiently detect light or a structure able to improve light intensity because the intensity of light irradiating from a light source is small (from equations 1 to 3),
3) since optical path should be long for sensitivity of an infrared gas sensor to generate high output voltages at identical densities, optical structures should be manufactured to have a path as long as possible, and in this instance, a state that may minimize amount absorbed when reflecting from a structure should be ensured by minimizing reflection from an optical structure,
4) and should be equipped with a characteristic of incident light arriving at an optical sensor part to be collected in the center of an optical sensor part in a radius as small as possible and should reach inside field of view of an optical sensor.

SUMMARY OF INVENTION

The objective of the present invention is to provide an optical wave guide having multiple independent optical path and optical gas sensor using that that may condense light irradiating from a light source within tens~hundreds μm radius (in other words, Field of View) from center of an optical sensor part without using a separate condenser.

Another objective of the present invention is to provide an optical wave guide having multiple independent optical path and optical gas sensor using that that reduces loss of amount of light and at the same time allows light to condense properly to an optical sensor part by realizing a structure with a long optical path and a structure minimizing reflection of light.

Another objective of the present invention is to provide an optical wave guide having multiple independent optical path and optical gas sensor using that that may actively deal with secular change of a light source.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 9A:
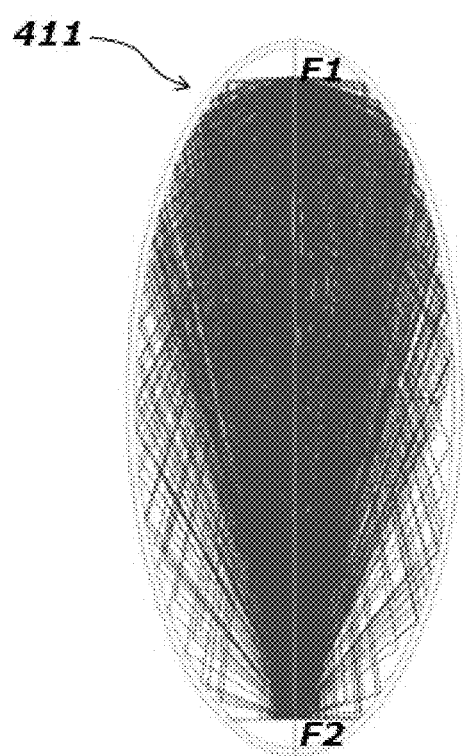
FIG. 9A illustrates optical path of light irradiating from a light source positioned at a first focal point in a 3-dimension elliptical mirror and light flux arriving at an optical sensor part positioned in a second focal point.
Figure 9B:
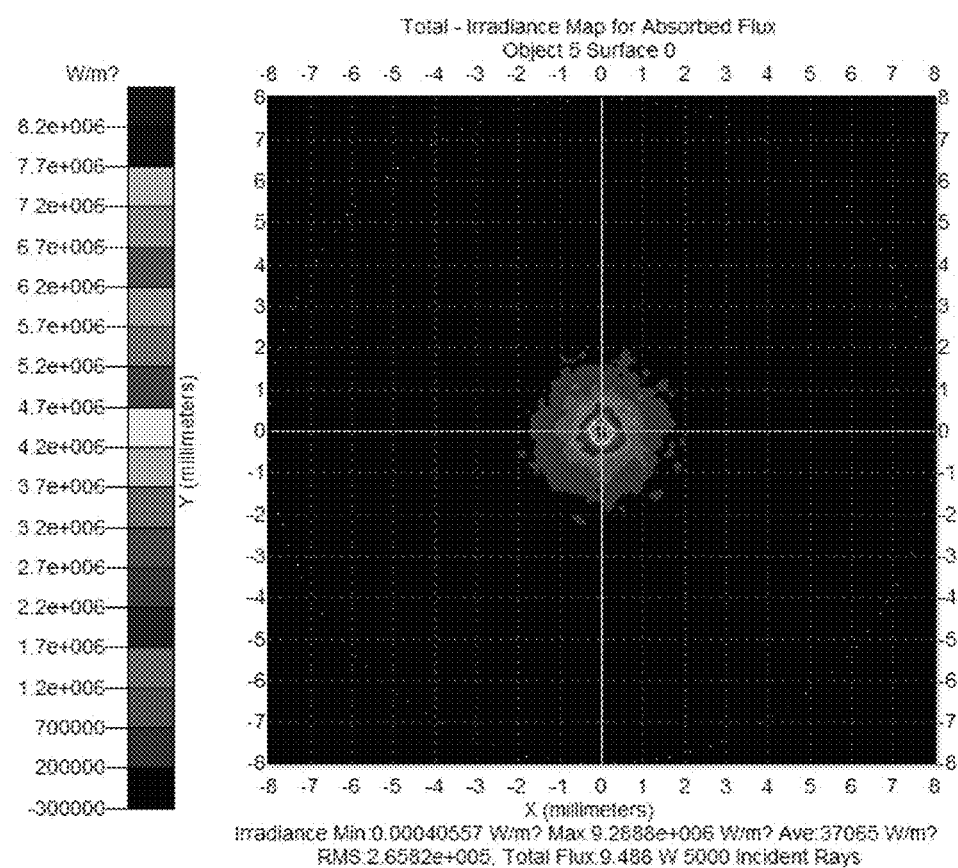
FIG. 9B illustrates results of simulation of a shape of light flux arriving at an optical sensor part.

As illustrated in FIG. 9A, after light (i.e. infrared ray (3.4 µm) is assumed) irradiating from a light source positioned at a first focal point (F1) of a 3 dimensional elliptical mirror (411) reflects once at an inside wall of a 3 dimensional elliptical mirror (411), it reaches an optical sensor part positioned at a second focal point (F2) of a 3 dimensional elliptical mirror (411). Referring to FIG. 9B, 100% of infrared ray irradiating from a light source positioned at a first focal point (F1) of a 3 dimensional elliptical mirror (411) reaches an optical sensor part positioned at a second focal point (F2) of a 3 dimensional elliptical mirror (411), and shows excellent characteristics of condensing maximum energy per unit area of an arriving light flux in an 1 mm radius.

When an optical wave guide for use for optical gas sensors is made in a shape of a 3 dimensional ellipsoid, even though volume increases, since all of the light irradiating from a light source positioned at a first focal point (F1) of a 3 dimensional elliptical mirror (411) is all condensed at an optical sensor part positioned at a second focal point (F2) of a 3 dimensional elliptical mirror (411), there is almost no loss of light. Also, incident light to an optical sensor part positioned at a second focal point (F2) of a 3 dimensional elliptical mirror is incident on a small concentric circle with a radius of tens~hundreds of µm, and thus it is effective to manufacture filters, which is a standard component of an optical sensor part, and a structure in which it is able to accurately reach an infrared ray sensing part positioned below a filter.

Figure 10A:
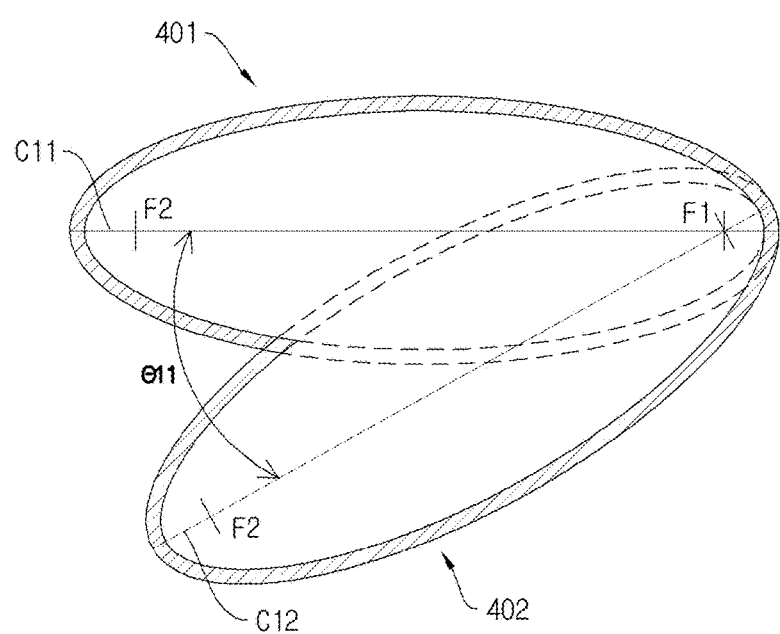
FIG. 10A illustrates an optical waveguide having multiple independent optical path in accordance with the present invention is realized by two 3 dimension ellipsoids.
Figure 10B:
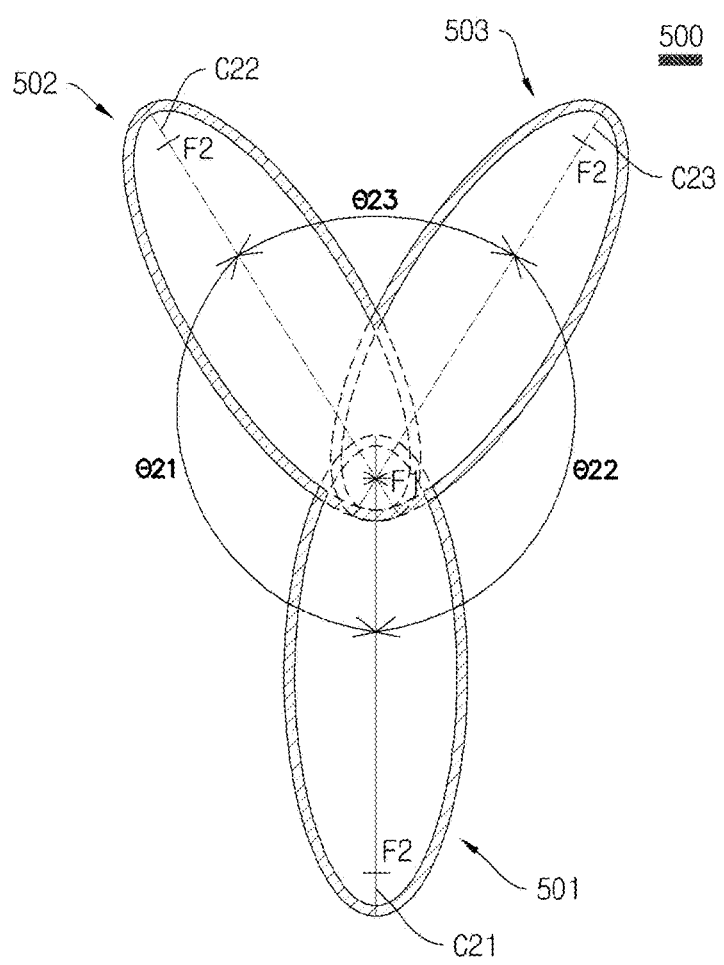
FIG. 10B illustrates an optical waveguide having multiple independent optical path in accordance with the present invention is realized by three 3 dimension ellipsoids.
Figure 10C:
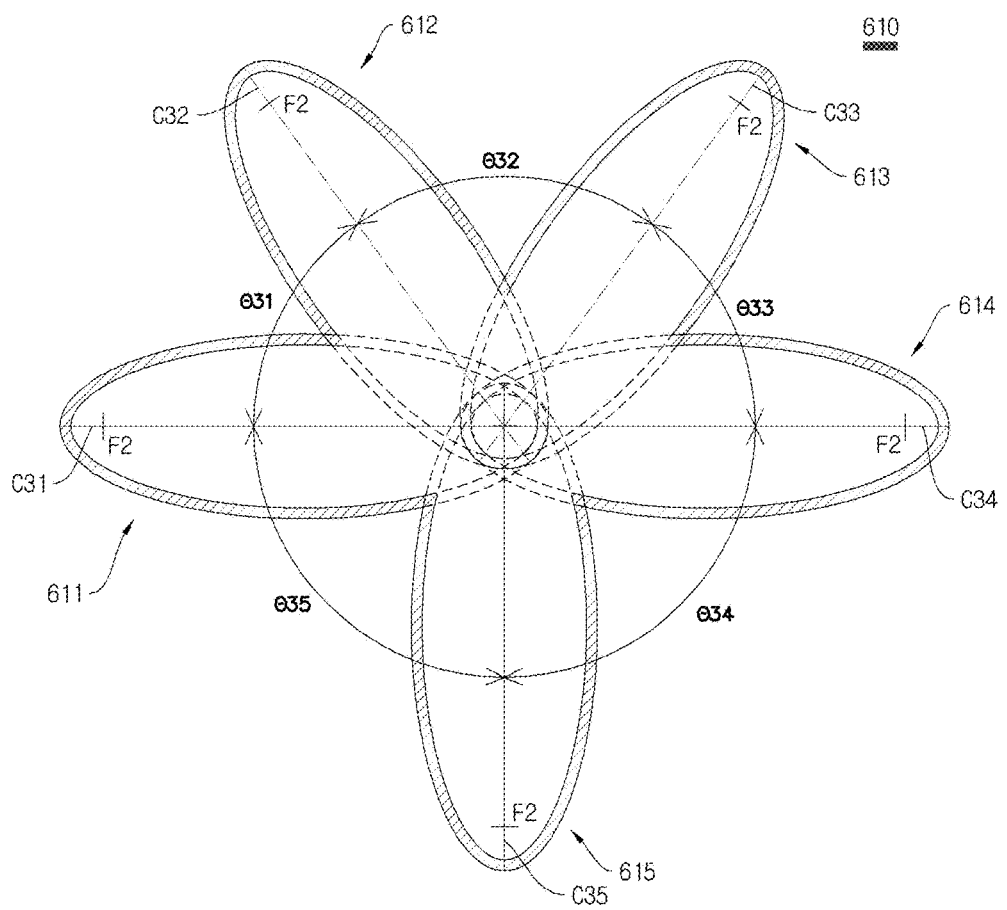
FIG. 10C illustrates an optical waveguide having multiple independent optical path in accordance with the present invention is realized by five 3 dimension ellipsoids.

FIG. 10A, FIG. 10B and FIG. 10C are exemplary drawings describing an optical wave guide having multiple independent optical path in accordance with the present invention. First, referring to FIG. 10A, it illustrates an optical wave guide having multiple independent optical path in accordance with the present invention is realized by two 3 dimension ellipsoids (401, 402). Two 3 dimension ellipsoids (401, 402) are realized so that they share each first focal points (F1) as a common focal point and virtual reference lines (C11, C12) connecting each first focal point (F1) and second focal point (F2) forms a constant angle (θ11).

When an optical wave guide having multiple independent optical path is realized by two 3 dimensional ellipsoids (401, 402), manly three installation positions for light source and optical sensor part may be intuitively assumed.

(1) A light source is installed at one of the second focal point (F2) of the two 3 dimensional ellipsoid (401, 402), (2) an optical sensor part is installed at a first focal point (F1), which is a common focal point, and light sources are installed at each of the second focal points (F2) of the two 3 dimensional ellipsoids (401, 402), (3) a light source is installed at a first focal point (F1), which is a common focal point, and optical sensors are installed at each of the second focal points (F2) of the two 3 dimensional ellipsoids (401, 402).

When an optical wave guide having multiple independent optical path is realized by two 3 dimensional ellipsoids (401, 402), installation positions for light sources and optical sensor parts are divided into the described three methods and results of simulation of shape of light flux arriving at optical sensor parts for each method is described below.

Referring to FIG. 10B, it illustrates an optical wave guide (500) having multiple independent optical path realized by three 3 dimensional ellipsoids (501, 502, 503). Three 3 dimensional ellipsoids (501, 502, 503) may be realized so that they share each first focal points (F1) as a common focal point and virtual reference lines (C21, C22, C23) connecting each first focal points (F1) and second focal points (F2) are at constant angles ($\theta 21$, $\theta 22$, $\theta 22$).

When an optical wave guide (500) having multiple independent optical path is realized by three 3 dimensional ellipsoids (501, 502, 503), mainly five installation positions for light sources and optical sensor parts may be intuitively assumed.

(1) A light source is installed at a common focal point, and optical sensors are installed at each of the second focal points (F2) of the three 3 dimensional ellipsoids (501, 502, 503).

(2) An optical sensor is installed at a common focal point, and light sources are installed at each of the second focal points (F2) of the three 3 dimensional ellipsoids (501, 502, 503).

(3) Optical sensors are installed at each of the second focal points (F2) of first and second ellipsoids (501, 502) of three 3 dimensional ellipsoids (501, 502, 503), and a light source installed at a second focal point (F2) of third ellipsoid (503), (4) An optical sensor is installed at a second focal point (F2) of a first ellipsoid (501) of three 3 dimensional ellipsoids (501, 502, 503), and light sources are installed at second focal points (F2) of second and third ellipsoids (502, 503), (5) A light source is installed at a second focal point (F2) of a first ellipsoid (501) of three 3 dimensional ellipsoids (501, 502, 503), and optical sensors are installed at second focal points (F2) of second and third ellipsoids (502, 503).

As an example, when an optical wave guide (500) having multiple independent optical path has an optical sensor installed at a first focal point (F1), which is a common focal point of three 3 dimensional ellipsoids (501, 502, 503), and light sources installed at each of the second focal points (F2) of the three 3 dimensional ellipsoids (501, 502, 503), it is preferable to select the third angle ($\theta 23$) formed by a virtual reference line (C22) connecting a first focal point and a second focal point of a second ellipsoid (502) and a virtual reference line (C23) connecting a first focal point and a second focal point of a third ellipsoid (503), to be from a range of 20 degrees or over and 60 degrees or below.

For another example, when an optical wave guide (500) having multiple independent optical path has light source installed at a second focal point (F2) of a second ellipsoid (502) of three 3 dimensional ellipsoids (501, 502, 503), and optical sensors installed at second focal points (F2) of each first and third ellipsoids (501, 503), it is preferable to select the third angle ($\theta 23$) formed by a virtual reference line (C22) connecting first focal point and second focal point of second ellipsoid (502) and a virtual reference line (C23) connecting first focal point and second focal point of third ellipsoid (503), to be from a range of 20 degrees or over and 60 degrees or below.

For another example, when an optical wave guide (500) having multiple independent optical path has optical sensors installed at second focal points (F2) of second and third ellipsoids (501, 502) of three 3 dimensional ellipsoids (501, 502, 503), and a light source installed at a second focal point (F2) of a first ellipsoid (503),), it is preferable to select the third angle ($\theta 23$) formed by a virtual reference line (C22) connecting first focal point and second focal point of second ellipsoid (502) and a virtual reference line (C23) connecting first focal point and second focal point of third ellipsoid (503), to be from a range of 20 degrees or over and 60 degrees or below.

Referring to FIG. 10C, it illustrates an optical wave guide (610) having multiple independent optical path realized by five 3 dimensional ellipsoids (611 to 615). Five 3 dimensional ellipsoids (611 to 615) may be realized so that they share each first focal points (F1) as a common focal point and virtual reference lines (C31 to C353) connecting each first focal points (F1) and second focal points (F2) are at constant angles ($\theta 31$ to $\theta 35$).

As can be seen in FIG. 10A, FIG. 10B and FIG. 10C, an optical wave guide having multiple independent optical path in accordance with the present invention may be realized by multiple ellipsoids sharing each first focal points as a common focal point and virtual reference lines connecting each first focal points and second focal points forming constant angles with each other.

Example 1 an optical wave guide is realized by two 3 dimensional elliptical mirrors, a light source is installed at a second focal point (F2) of one of the elliptical mirrors, and an optical sensor part is installed at a second focal point (F2) of another elliptical mirror.

Figure 11A:
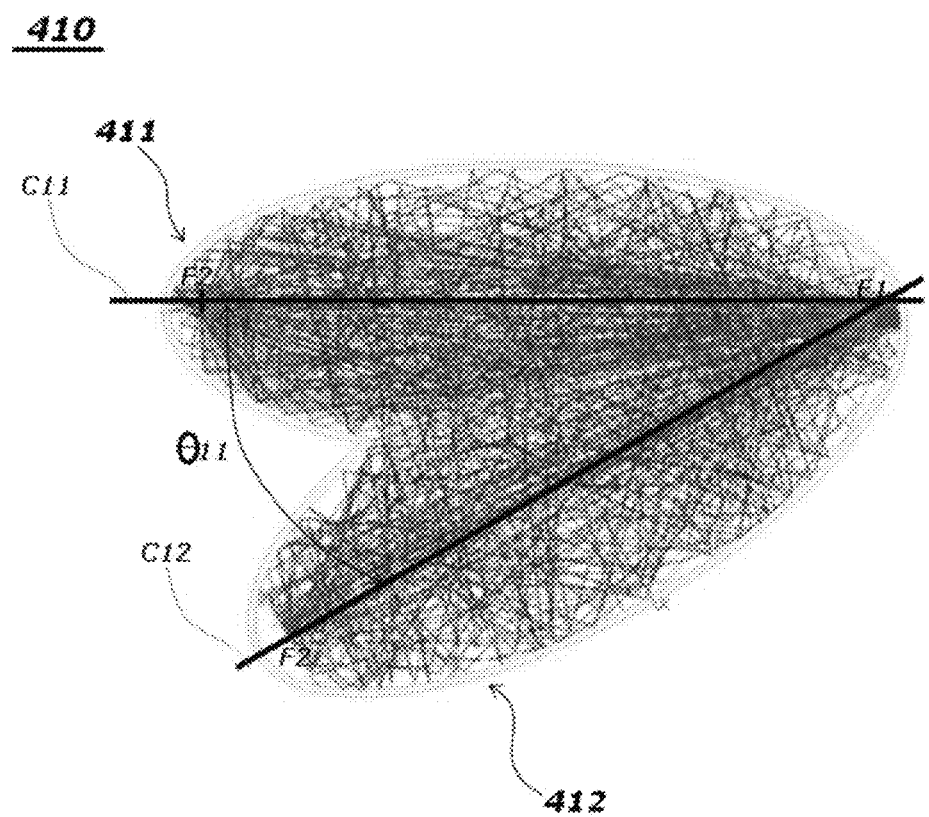
FIG. 11A is a drawing illustrating an optical path when an optical wave guide having multiple independent optical path in accordance with the present invention has two elliptical mirrors.
Figure 11B:
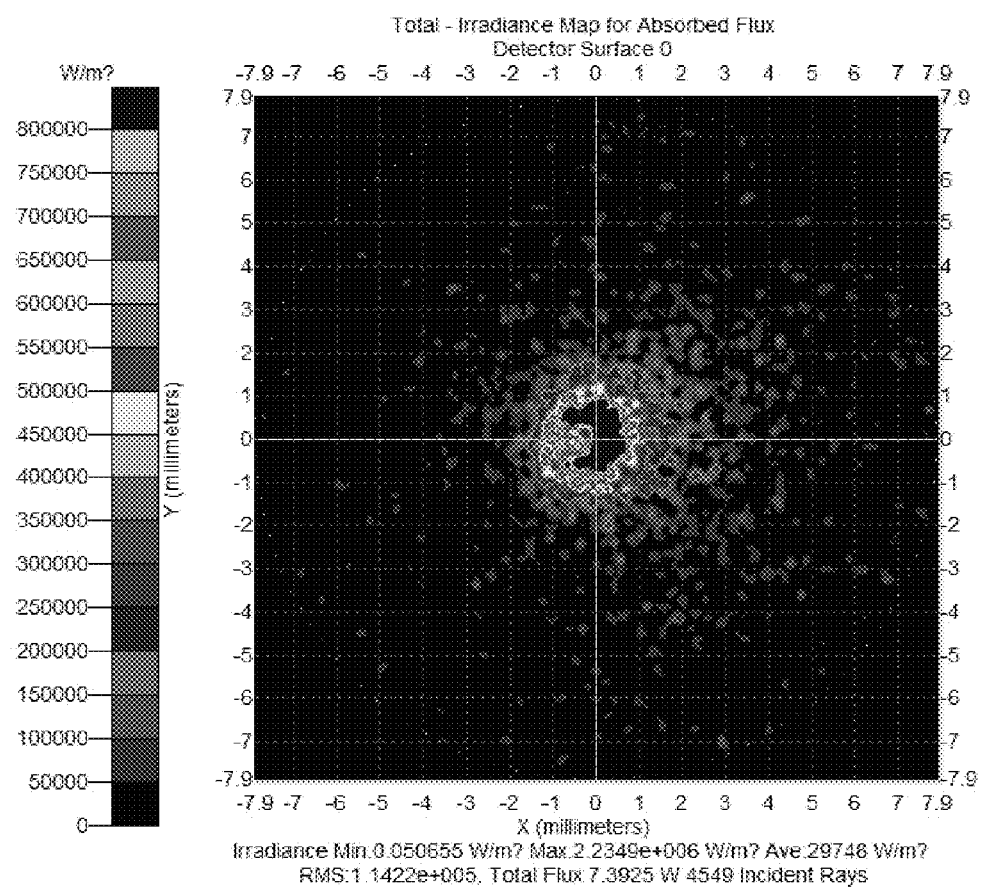
FIG. 11B illustrates results of simulation of a shape of a light flux arriving at an optical sensor part.
Figure 12:
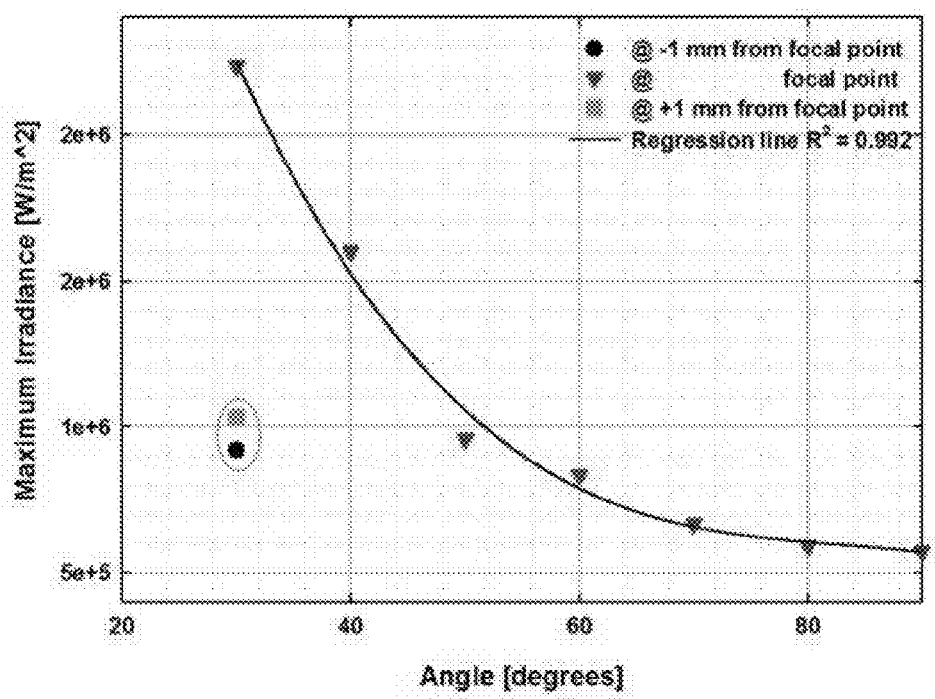
FIG. 12 illustrates energy of incident light per unit area according to angles between major axis of two 3 dimensional elliptical mirrors.
Figure 13A:
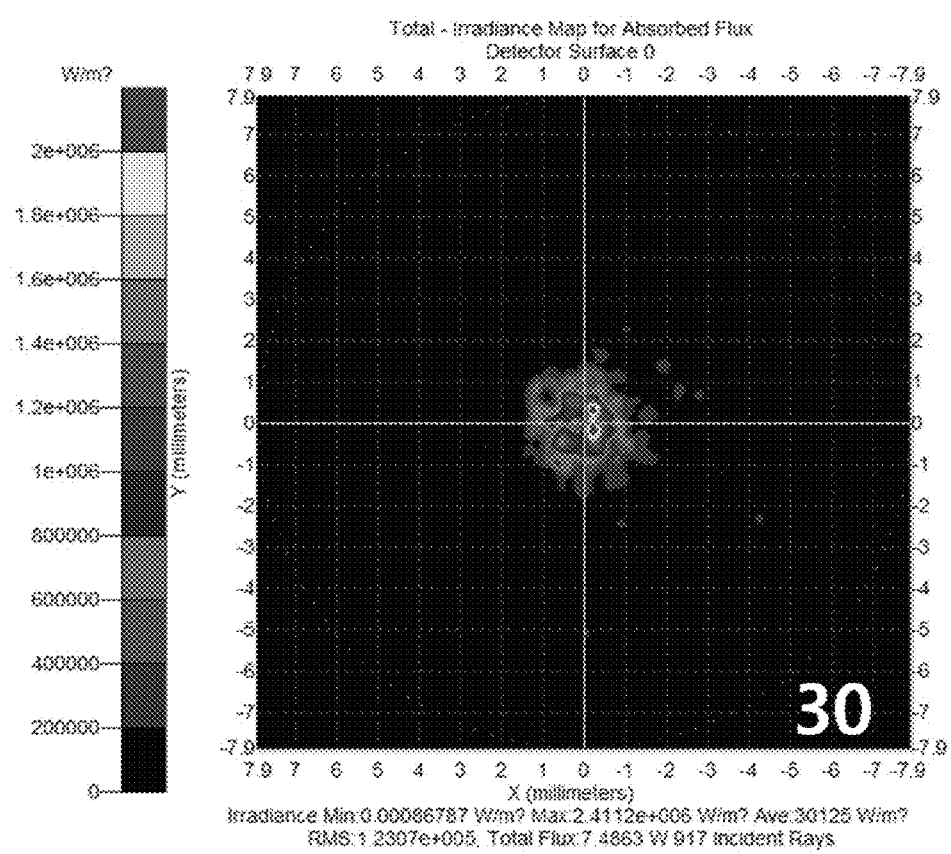
FIG. 13A illustrates a result of simulation of a shape of light flux arriving at an optical sensor part when angles between major axis of two 3 dimensional elliptical mirrors is 30 degree.
Figure 13B:
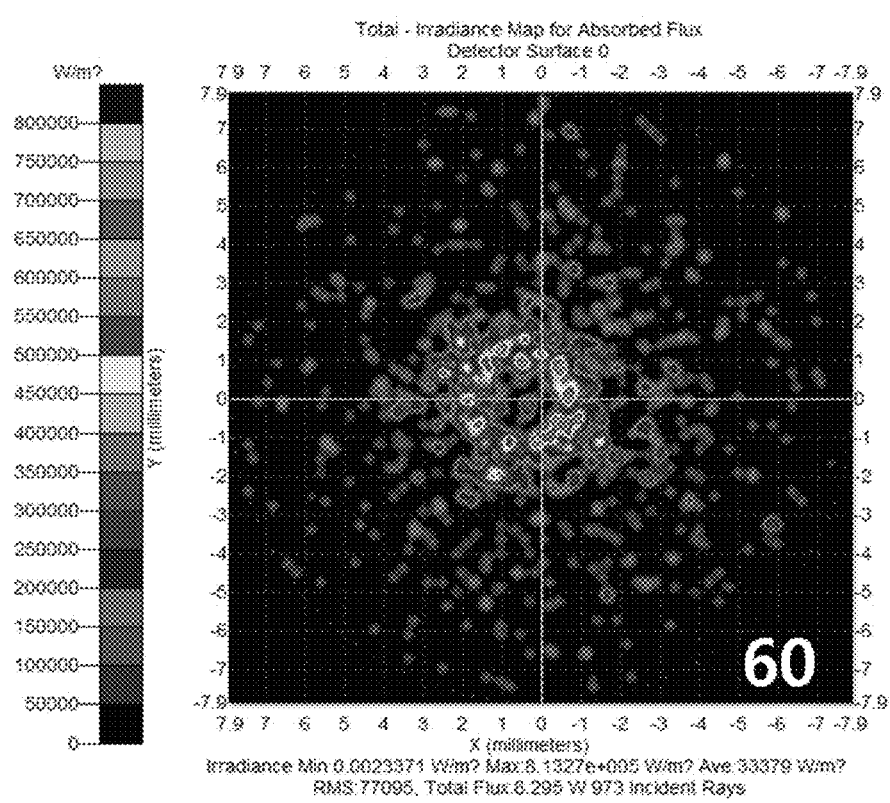
FIG. 13B illustrates a result of simulation of a shape of light flux arriving at an optical sensor part when angles between major axis of two 3 dimensional elliptical mirrors is 60 degree.
Figure 13C:
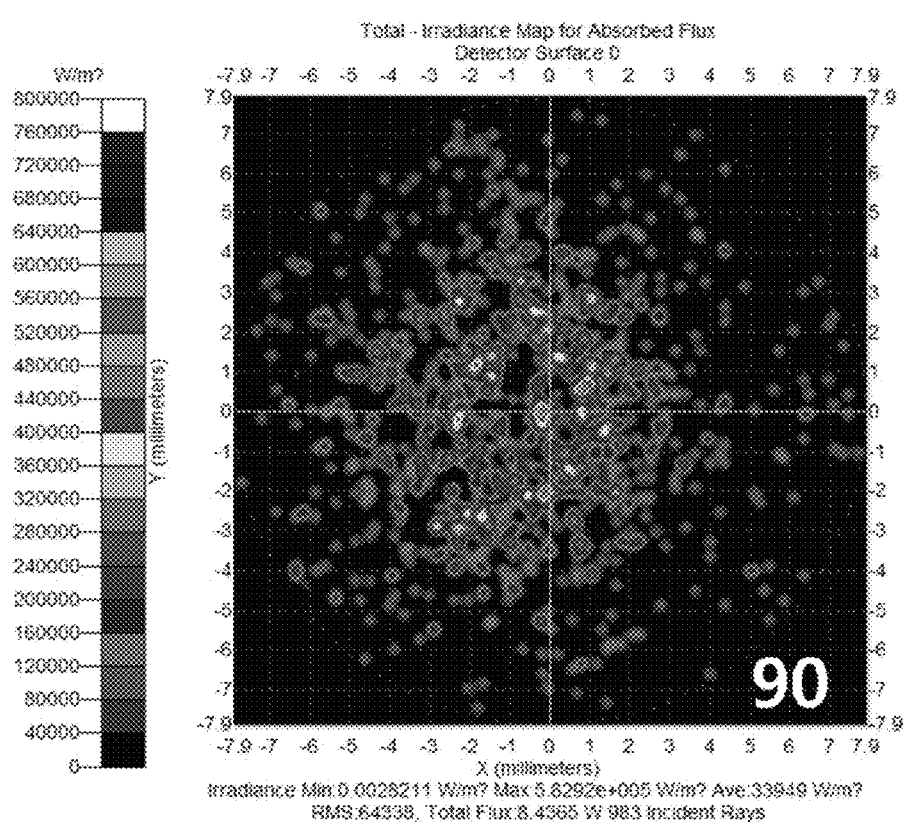
FIG. 13C illustrates a result of simulation of a shape of light flux arriving at an optical sensor part when angles between major axis of two 3 dimensional elliptical mirrors is 90 degree.
Figure 14:
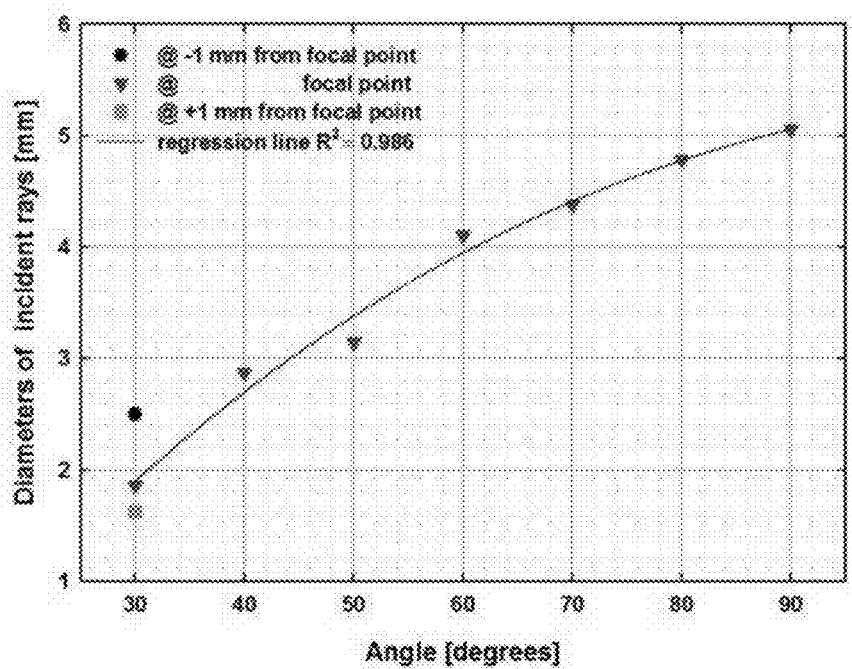
FIG. 14 illustrates relationship between radius of condensing of incident light arriving at an optical sensor part according to change in angles between major axis of two 3 dimensional elliptical mirrors

FIG. 11A is drawing illustrating an optical wave guide having multiple independent optical path in accordance with example 1 of the present invention, and FIG. 11B illustrates results of simulation of shape of light flux arriving at an optical sensor part, and FIG. 12 illustrates energy of incident light per unit area according to angles between major axis of two 3 dimensional elliptical mirrors, and FIG. 13A, FIG. 13B and FIG. 13C illustrate results of simulation of shape of light flux arriving at an optical sensor part according to angles between major axis of two 3 dimensional elliptical mirrors, and FIG. 14 illustrates relationship between radius of condensation of incident light arriving at an optical sensor part according to change in angles between major axis of two 3 dimensional elliptical mirrors.

First, referring to FIG. 11A, it illustrates an optical wave guide having multiple independent optical path realized by two 3 dimensional elliptical mirrors (411, 412). Two 3 dimension elliptical mirrors (411, 412) are realized so that they share each first focal points (F1) as a common focal point and virtual reference lines (C11, C12) connecting each first focal point (F1) and second focal point (F2) form a constant angle ($\theta 11$).

An optical wave guide (410) having multiple independent optical path in accordance with FIG. 11A has a light source installed at a second focal point (F2) of a first elliptical mirror (411), and an optical sensor installed at a second focal point (F2) of a second elliptical mirror (412). In this case, optical path of incident light irradiating from a light source installed at a second focal point (F2) of a second elliptical mirror (412) to an optical sensor part installed at a second focal point (F2) of a second elliptical mirror (41) is as FIG. 11A.

Results of simulation of shape of light flux arriving at an optical sensor part installed at a second focal point (F2) of a second elliptical mirror (412) is illustrated in FIG. 11B, simulation was performed assuming 30 degrees for an angle ($\theta 11$) between virtual reference lines (C11, C12) and 16 mm for diameter of an optical sensor part. Light flux arriving at an optical sensor part is about 95% (4,549 of 5,000) of irradiating light, and arrived light condensed in a radius of about 2 mm may be observed. For an optical wave guide (410) having multiple independent optical path, it is preferable to select the angle formed by a virtual reference line connecting a first focal point and a second focal point of a first ellipsoid (411) and a virtual reference line connecting a first focal point and a second focal point of a second ellipsoid (412), to be from a range of 10 degrees or over and 20 degrees or below.

When a light source is installed at a second focal point (F2) of a first elliptical mirror (411), and an optical sensor is installed at a second focal point (F2) of a second elliptical mirror (412), energy of incident light per unit area according to an angle (θ11) between two virtual reference lines (C11, C12) of two 3 dimensional elliptical mirrors (411, 412) is illustrated as FIG. 12. As FIG. 12, as angle (θ11) between two virtual reference lines (C11, C12) of two 3 dimensional elliptical mirrors (411, 412) becomes greater, energy of incident light irradiating from a light source arriving at an optical sensor part reduces exponentially, and angles (θ11) of over 50 degrees between virtual reference lines (C11, C12) showing a difference of light intensity of square of about 1 or more than that of a structure with 30 degrees may be observed.

But, even if an optical wave guide (410) with an angle (θ11) between two virtual reference lines (C11, C12) of 30 degrees is manufactured, if a light source, which should be installed at a second focal point (F2) of a first elliptical mirror (411), deviates ±1 mm from a second focal point (F2) by an error in manufacturing process or assembly, it may be predicted that it may show signs of energy of incident light to an optical sensor part positioned at a second focal point (F2) of a second elliptical mirror (412) reducing by a square of about 1 or more—here, shows an energy state almost similar to a structure with an angle (θ11) of over 50 degrees between virtual reference lines (C11, C12)—so careful attention during manufacturing process is required.

FIG. 13A, FIG. 13B and FIG. 13C illustrate results of simulation of shape of optical flux arriving at an optical sensor part according to angles between major axis of two 3 dimensional elliptical mirrors (411, 412) when a light source is installed at a second focal point (F2) of a first elliptical mirror (411) and an optical sensor is installed at a second focal point (F2) of a second elliptical mirror (412). As can be seen in FIG. 13A, FIG. 13B and FIG. 13C, as angles between major axis of two 3 dimensional elliptical mirrors (411, 412) becomes greater as 30 degrees, 60 degrees, 90 degrees, light flux arriving at an optical sensor part does not condense but spreads. It may be observed that this describes, as illustrated in FIG. 12, as angle (θ11) between two virtual reference lines (C11, C12) of two 3 dimensional elliptical mirrors (411, 412) becomes greater, the phenomenon that density of optical energy per unit area arriving at an optical sensor part of light irradiating from a light source decreases.

FIG. 14 illustrates relationship between radius of condensation of incident light arriving at an optical sensor part according to change in angles between major axis of two 3 dimensional elliptical mirrors (411, 412) when a light source is installed at a second focal point (F2) of a first elliptical mirror (411), and an optical sensor is installed at a second focal point (F2) of a second elliptical mirror (412). This shows signs of diameter of incident light flux on an optical sensor part increasing as angles between major axis of two 3 dimensional elliptical mirrors (411, 412) become greater. This illustrates that when a light source, which should be installed at a second focal point (F2) of a first elliptical mirror (411), deviates ±1 mm from a second focal point (F2), diameter of light flux decreases or increases.

When putting above results together, it illustrates that even when manufacturing error of a light source, which should be installed at a second focal point (F2) of a first elliptical mirror (411), deviating ±1 mm from a second focal point (F2) occur, a focal point of a light source set to a positive direction from a second focal point (F2) of a first elliptical mirror (411) is relatively less influential to optical sensor manufacturing and characteristics than manufacturing error occurring in a negative direction.

Example 2 an optical wave guide is realized by two 3 dimensional elliptical mirrors, an optical sensor part is installed at a first focal point (F1), which is a common focal point, and light sources are installed at each second focal points (F2) of two 3 dimensional elliptical mirrors As in example 2, when an optical wave guide is configured, it is difficult to condense light irradiating from two light sources within tens~hundreds μm radius (in other words, Field of View) from the center of an optical sensor part. The reason is that light irradiating from two light sources causes interference.

Figure 15:
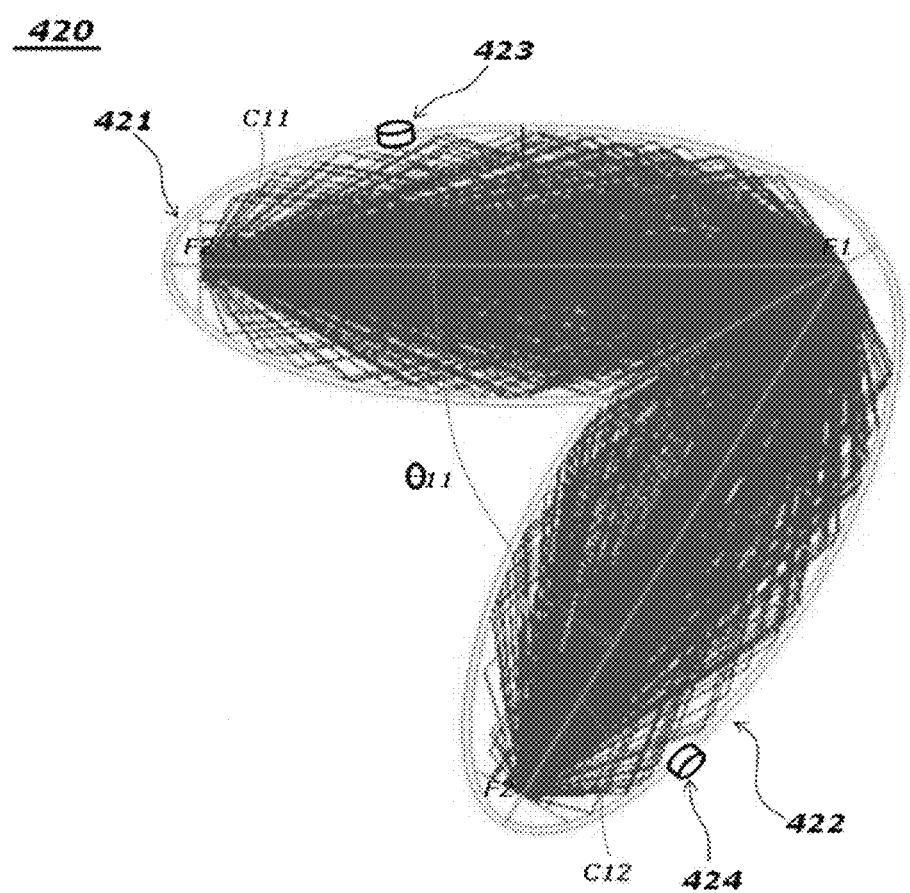
FIG. 15 illustrates optical path when an optical wave guide having multiple independent optical path in accordance with the present invention has two elliptical mirrors.
Figure 16A:
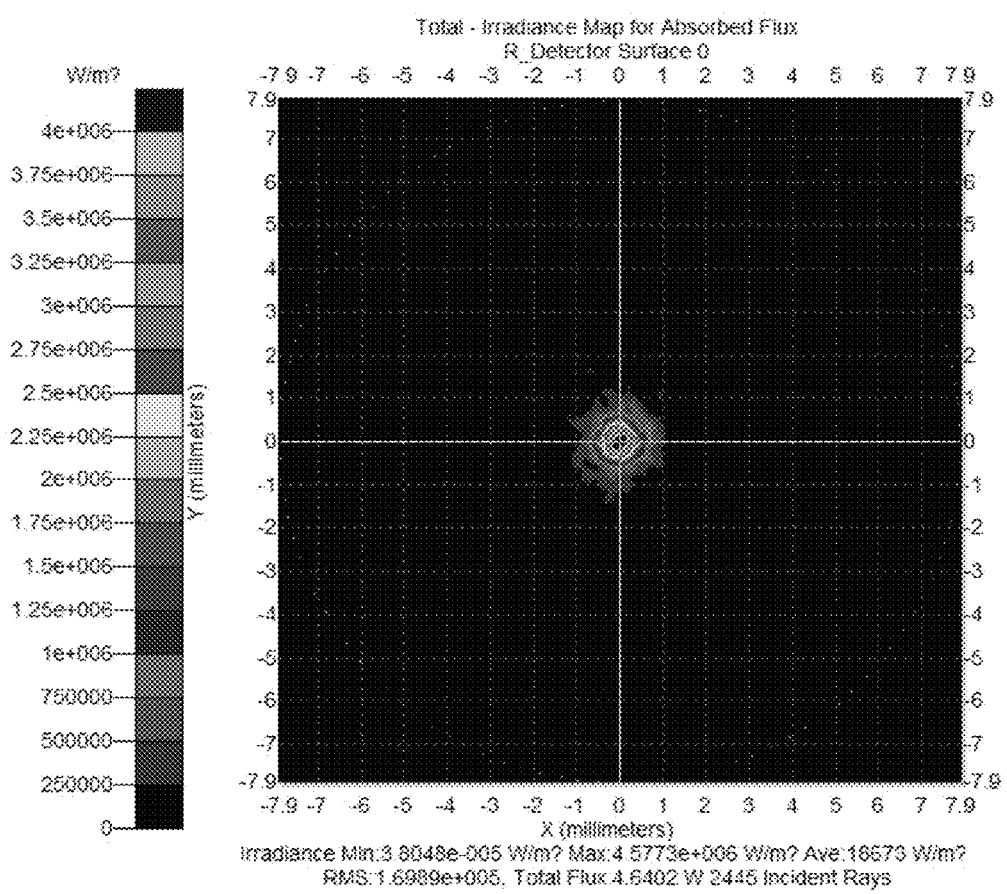
FIG. 16A illustrates a result of simulation of energy of light per unit area arriving at left side according to change in angles between major axis of two 3 dimensional elliptical mirrors according to structure illustrated in FIG. 15.
Figure 16B:
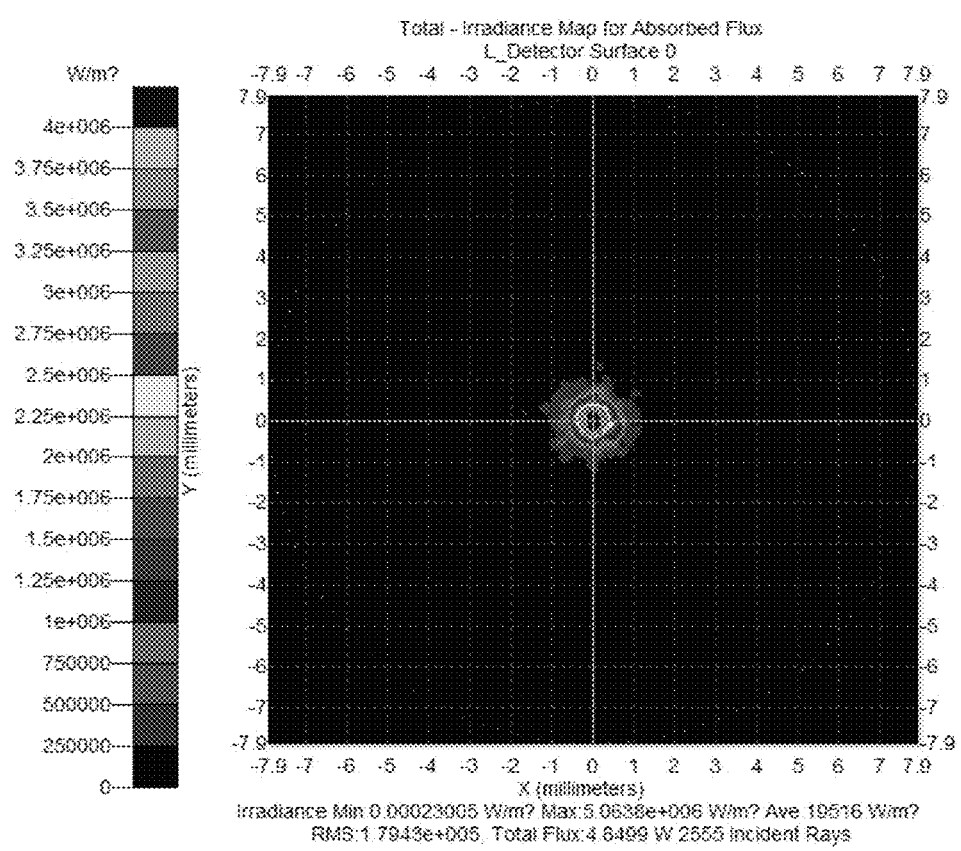
FIG. 16B illustrates a result of simulation of energy of light per unit area arriving at right side according to change in angles between major axis of two 3 dimensional elliptical mirrors according to structure illustrated in FIG. 15.
Figure 17:
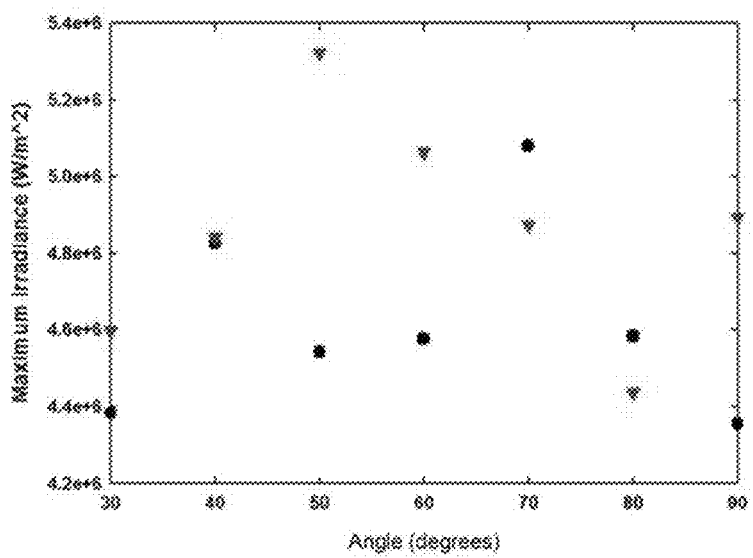
FIG. 17 illustrates results of simulation of energy of light per unit area arriving at left side and right side according to change in angles between major axis of two 3 dimensional elliptical mirrors according to structure illustrated in FIG. 15.
Figure 18A:
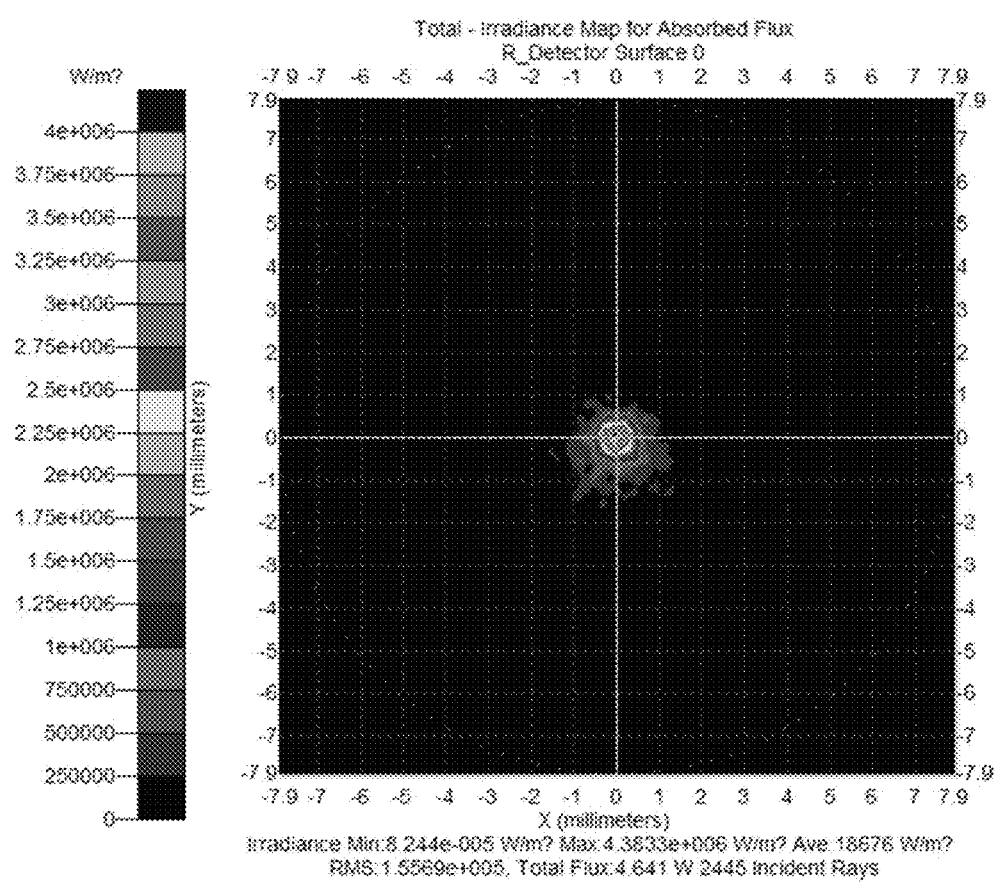
FIG. 18A illustrates a shape of light flux of an incident light arriving at an optical sensor part when angles between major axis according to structure illustrated in FIG. 15 is 30 degree.
Figure 18B:
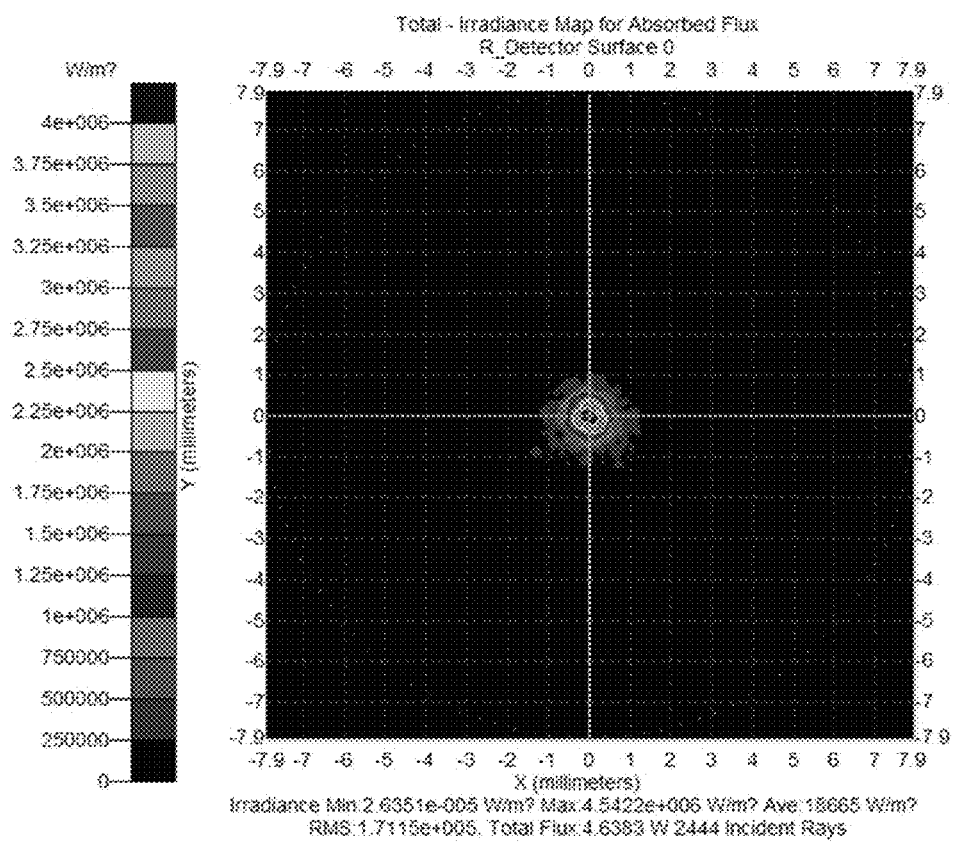
FIG. 18B illustrates a shape of light flux of an incident light arriving at an optical sensor part when angles between major axis according to structure illustrated in FIG. 15 is 50 degree.
Figure 18C:
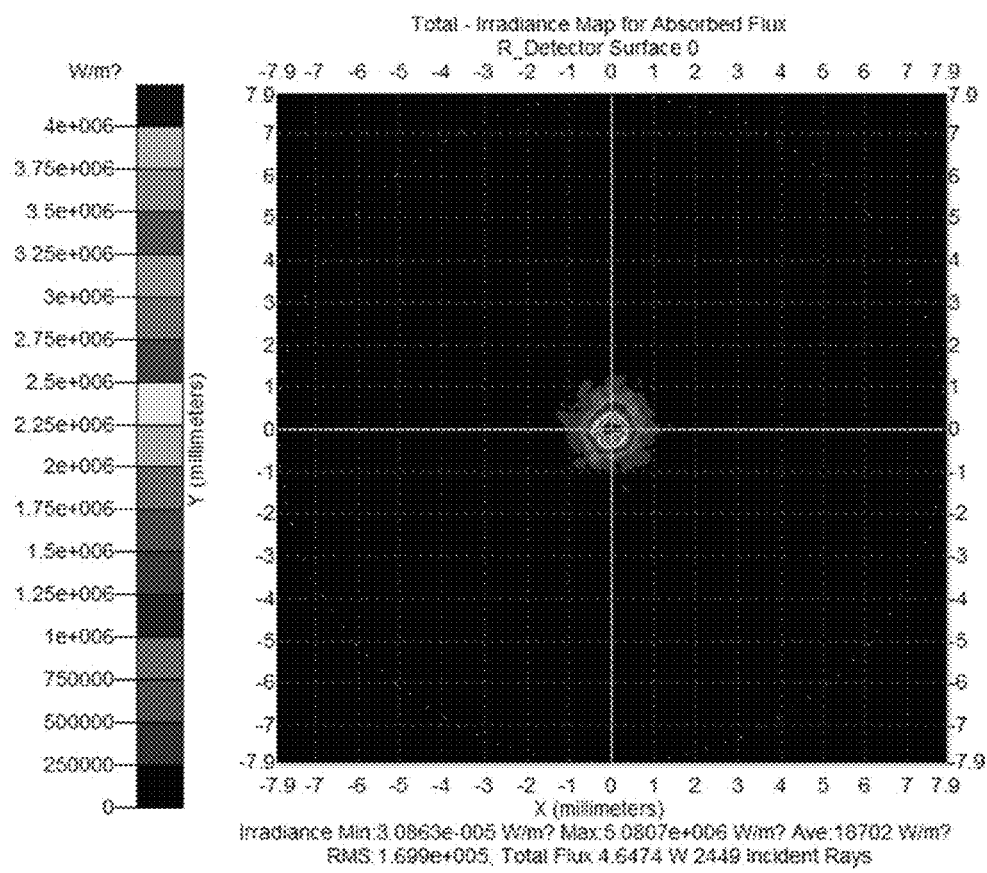
FIG. 18C illustrates a shape of light flux of an incident light arriving at an optical sensor part when angles between major axis according to structure illustrated in FIG. 15 is 70 degree.
Figure 18D:
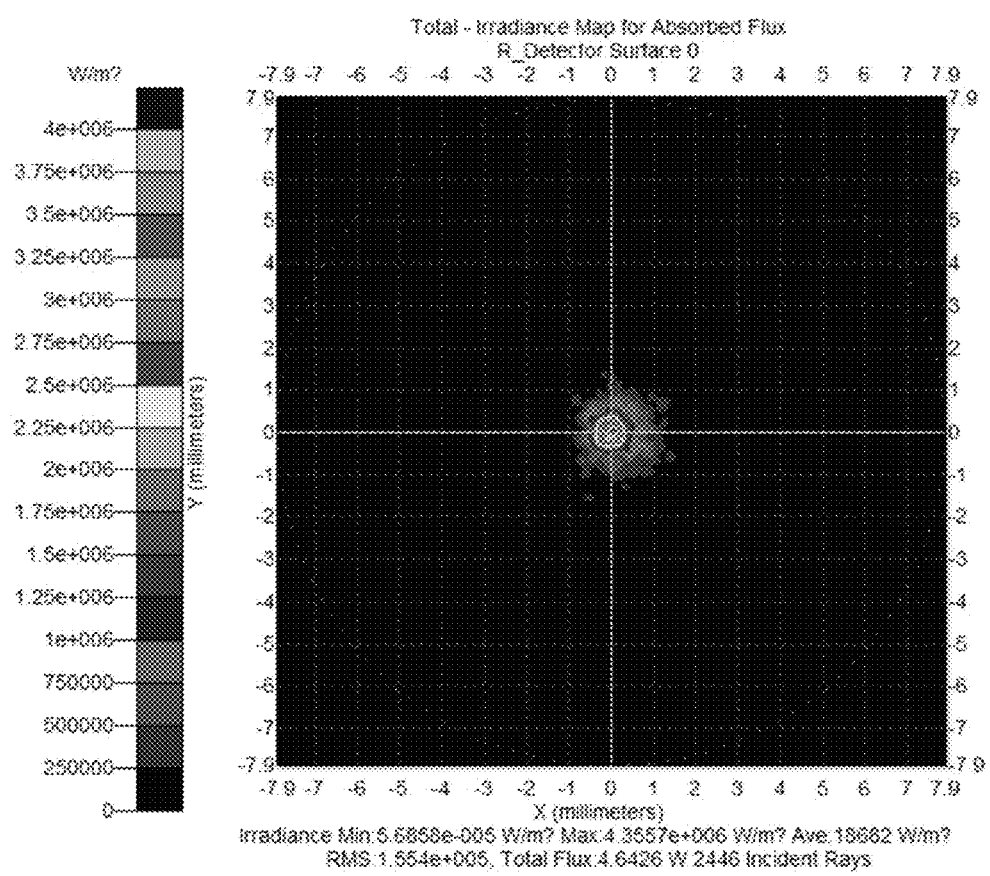
FIG. 18D illustrates a shape of light flux of an incident light arriving at an optical sensor part when angles between major axis according to structure illustrated in FIG. 15 is 90 degree.

Example 3 an optical wave guide is realized by two 3 dimensional elliptical mirrors, a light source is installed at a first focal point (F1), which is a common focal point, and optical sensor parts are installed at each second focal points (F2) of two 3 dimensional elliptical mirrors FIG. 15 illustrates optical paths when an optical wave guide having multiple independent optical path in accordance with the present invention has two elliptical mirrors, FIG. 16A, FIG. 16B and FIG. 17 illustrate results of simulation of energy of light per unit area arriving at a left side and right side according to change in angles between major axis of 3 dimensional elliptical mirrors according to structure illustrated in FIG. 15, FIG. 18A, FIG. 18B, FIG. 18C and FIG. 18D illustrate a shape of an optical flux of an incident light arriving at an optical sensor part according to change in angles between major axis according to structure illustrated in FIG. 15.

First, referring to FIG. 15, it illustrates an optical wave guide (420) having multiple independent optical path realized by two elliptical mirrors (421, 422). Two 3 dimension elliptical mirrors (421, 422) are realized so that they share each first focal points (F1) as a common focal point and virtual reference lines (C11, C12) connecting each first focal points (F1) and second focal points (F2) form a constant angle (θ11).

An optical wave guide (420) having multiple independent optical path in accordance with FIG. 15 has a light source installed at a first focal point (F1), which is a common focal point, and optical sensors installed at each of the second focal points (F2) of the two 3 dimensional elliptical mirrors (421, 422). In this case, optical path of incident light irradiating from a light source installed at a first focal point (F1) of a first elliptical mirror (421) to optical sensor parts installed at each second focal points (F2) of two 3 dimensional elliptical mirrors (421, 422) is as FIG. 15. As illustrated in FIG. 16A and FIG. 16B, it can be observed that light flux arriving at optical sensor parts installed at each second focal points (F2) of two 3 dimensional elliptical mirrors (421, 422) are all identical and the diameter is 2 mm or smaller.

FIG. 17 illustrates results of simulation of energy of light per unit area arriving at a left side and a right side according to angles between major axis of 3 dimensional elliptical mirrors according to structure illustrated in FIG. 15. As can be seen in FIG. 17, energy per unit area of incident light arriving at optical sensor parts installed at each second focal points (F2) of two 3 dimensional elliptical mirrors (421, 422) shows an aspect of being irrelevant to angles between major axis of two 3 dimensional elliptical mirrors (421, 422), and the difference of energy arriving at optical sensor parts installed at each second focal points (F2) of two 3 dimensional elliptical mirrors (421, 422) shows a maximum of under 10%.

Therefore, in can be observed that when optical sensor parts to measure gas with similar absorption bands (i.e. HC series, carbon monoxide, carbon dioxide) is installed at one of the second focal points (F2), sensing characteristics of sensor improves, and when one side is used as a reference for compensating for amount of light, since sensing of sensor is compensated without additional separate light sources, long-term reliability may be improved.

When an optical wave guide (420) having multiple independent optical path has a light source is installed at a first focal point (F1), which is a common focal point, and optical sensors are installed at each of the second focal points (F2) of the two 3 dimensional elliptical mirrors (421, 422), as can be seen in FIG. 18A, FIG. 18B, FIG. 18C and FIG. 18D, incident light arriving at optical sensor parts installed at each of the second focal points (F2) of the two 3 dimensional elliptical mirrors (421, 422) shows characteristics of condensing within a diameter of 2 mm of an optical sensor part irrelevant to change in angles between main axis of two 3 dimensional elliptical mirrors (421, 422).

As illustrated in FIG. 15, an optical wave guide (420) having multiple independent optical path comprises, on side parts of two 3 dimensional mirrors (421, 422), a gas inlet (423), to which gas flows into, installed where spacial density of light emitting from a light source is low and a gas outlet (424) installed separated from the gas inlet (423), and gas inlet and gas outlet of the optical wave guide maintains sealing.

Example 4: When an Optical Wave Guide is Realized by Three Elliptical Mirrors

Figure 19:
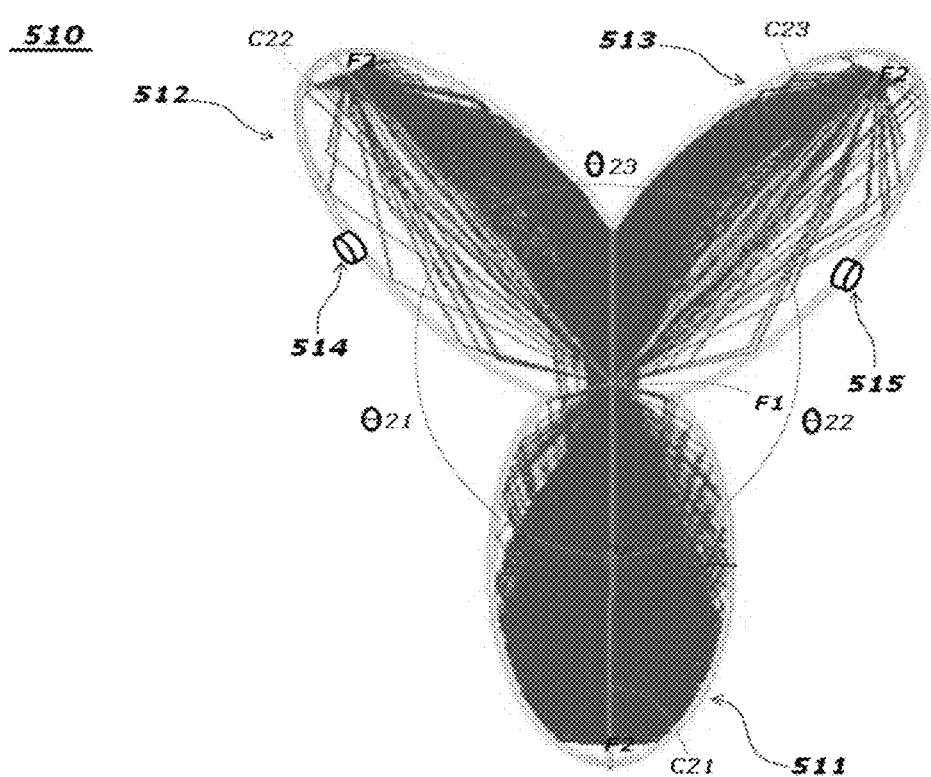
FIG. 19 illustrate structure and optical path of three 3 dimensional elliptical mirrors.
Figure 20:
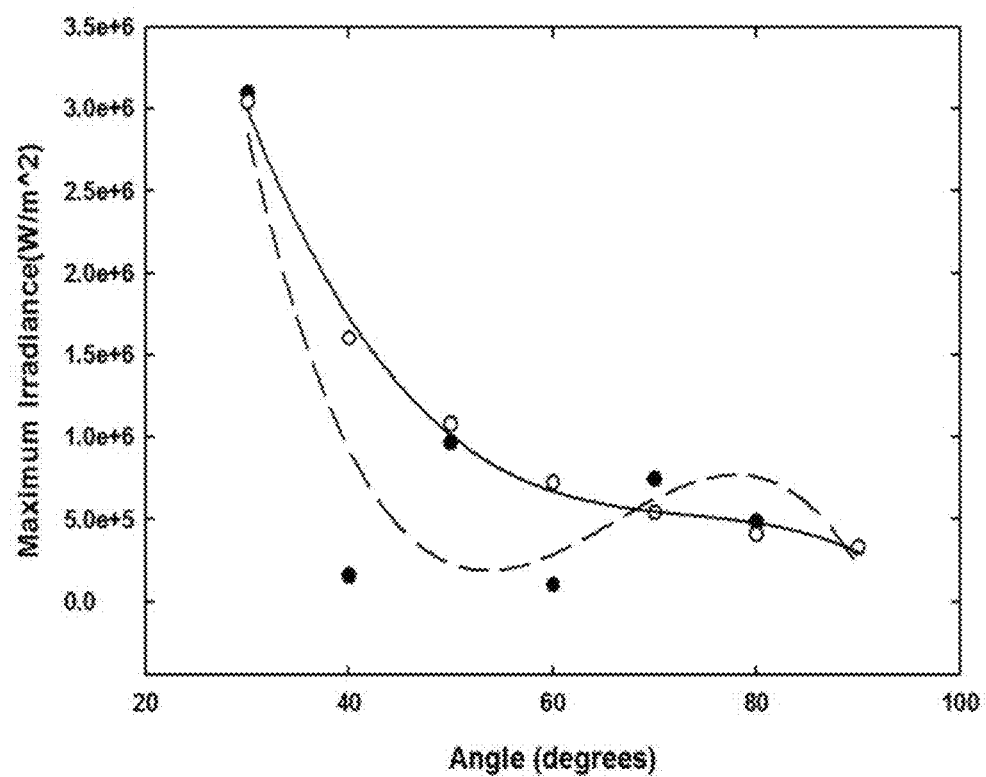
FIG. 20 illustrates results of simulation of energy of light per unit area arriving at an optical sensor part according to angles of major axis of upper two 3 dimensional elliptical mirrors illustrated in FIG. 19.
Figure 21:
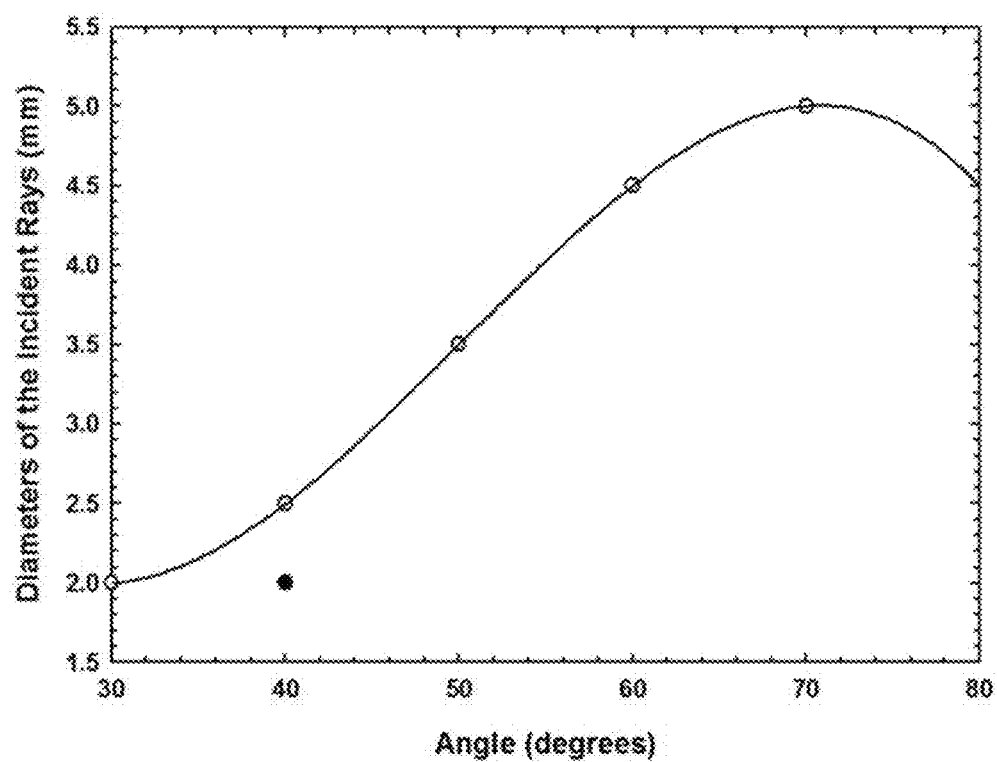
FIG. 21 illustrates change in diameter of incident light flux arriving at an optical sensor part according to angles of major axis of 3 dimensional elliptical mirrors illustrated in FIG. 19.
Figure 22A:
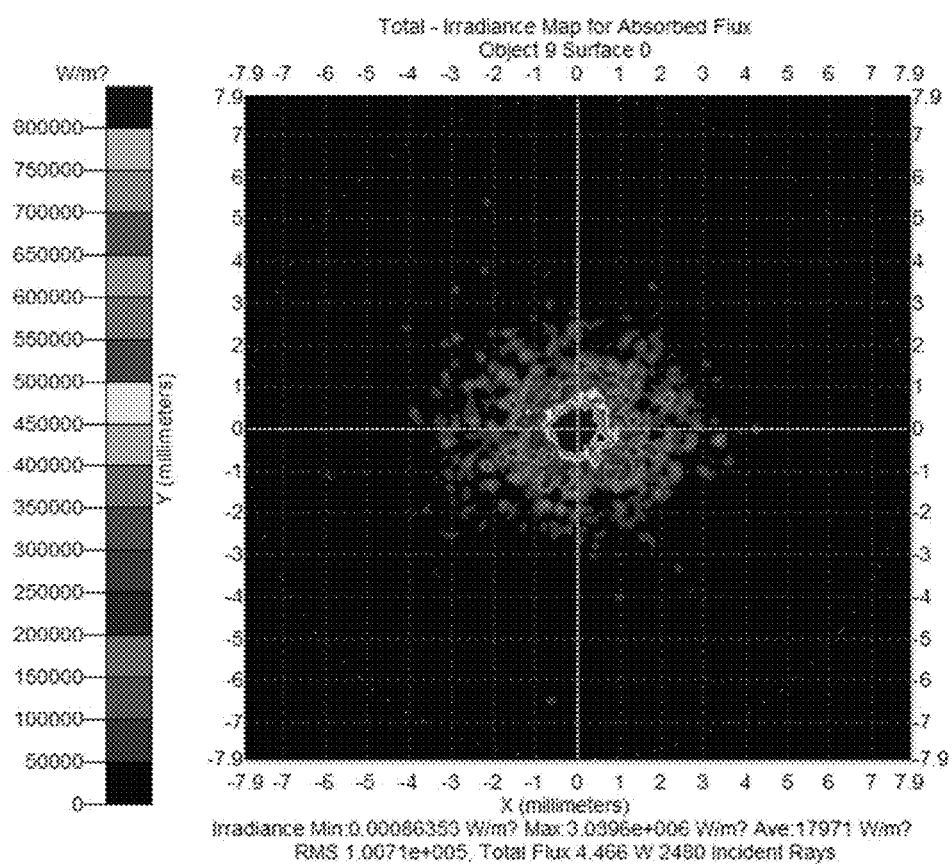
FIG. 22A illustrates a shape of incident light flux arriving at an optical sensor part when angles between major axis according to a structure illustrated in FIG. 19 is 60 degree.
Figure 22B:
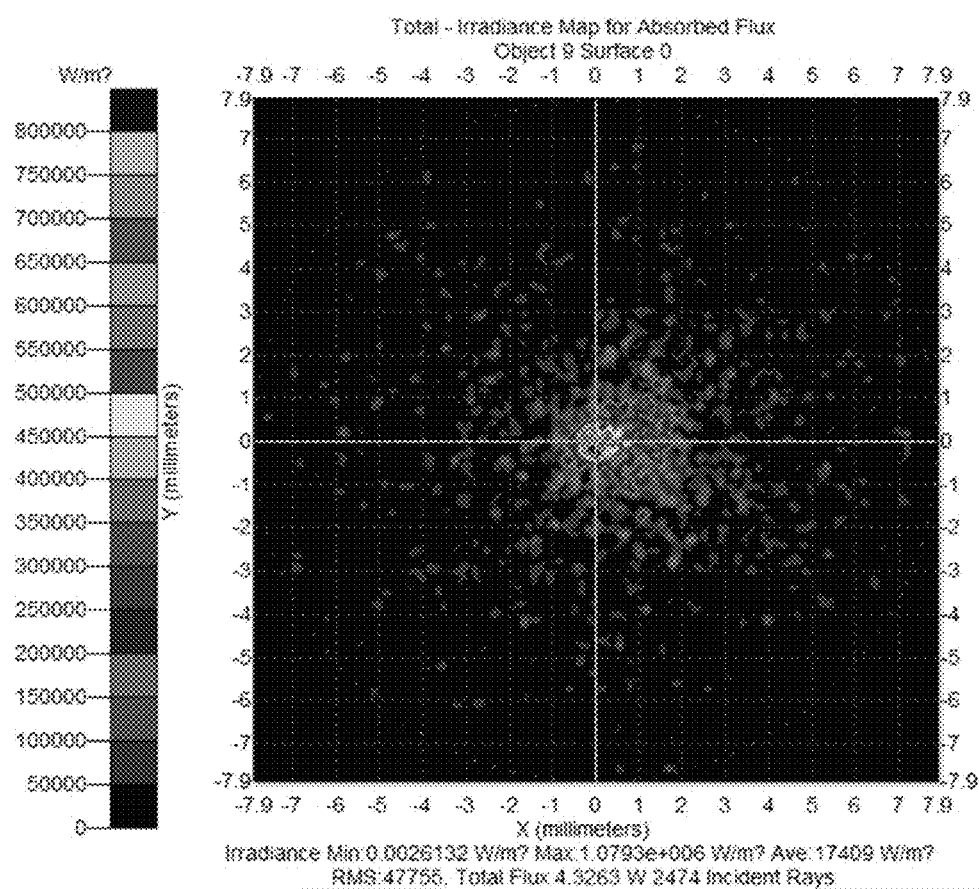
FIG. 22B illustrates a shape of incident light flux arriving at an optical sensor part when angles between major axis according to a structure illustrated in FIG. 19 is 100 degree.
Figure 22C:
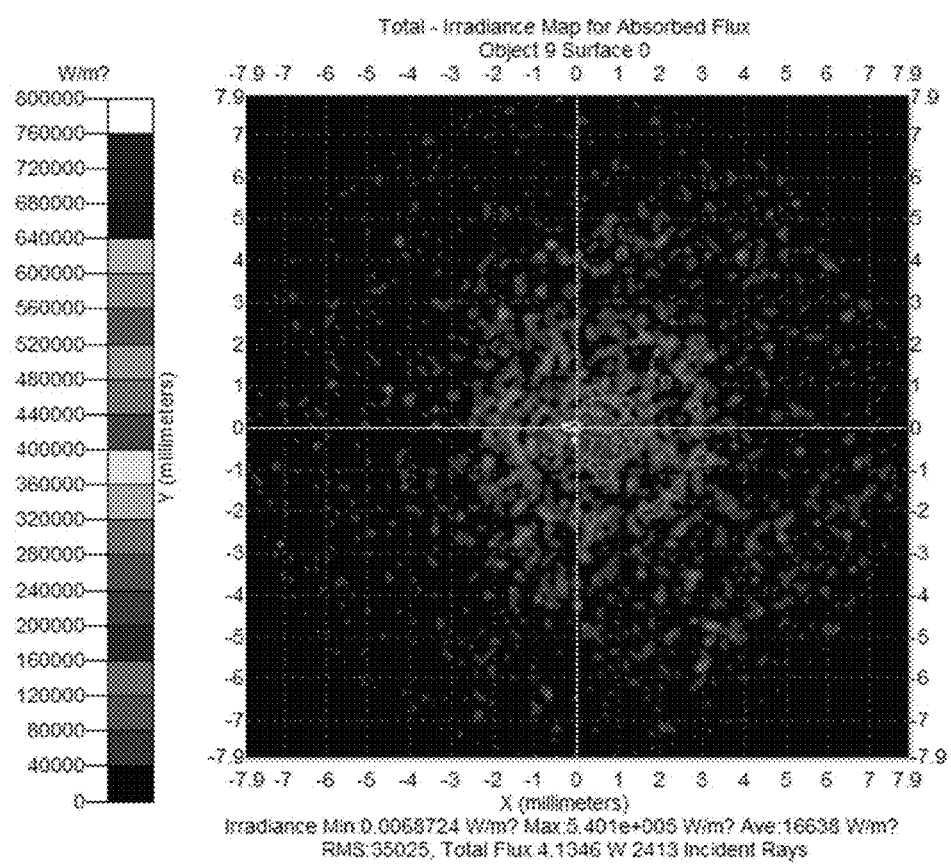
FIG. 22C illustrates a shape of incident light flux arriving at an optical sensor part when angles between major axis according to a structure illustrated in FIG. 19 is 140 degree.
Figure 22D:
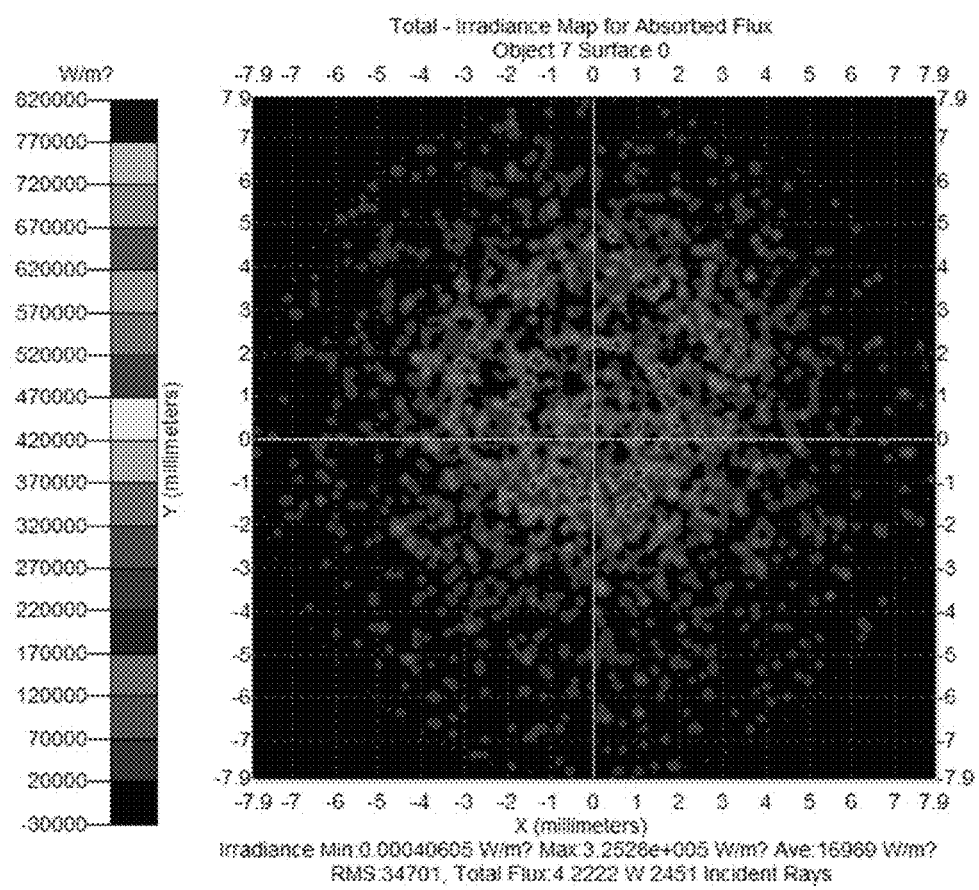
FIG. 22D illustrates a shape of incident light flux arriving at an optical sensor part when angles between major axis according to a structure illustrated in FIG. 19 is 180 degree.

FIG. 19 illustrate structure and optical path of three 3 dimensional elliptical mirrors, and FIG. 20 illustrates results of simulation of energy of light per unit area arriving at an optical sensor part according to angles of major axis of upper two 3 dimensional elliptical mirrors illustrated in FIG. 19, and FIG. 21 illustrates change in diameter of incident light flux arriving at an optical sensor part according to angles of major axis of 3 dimensional elliptical mirrors illustrated in FIG. 19, and FIG. 22A, FIG. 22B, FIG. 22C and FIG. 22D illustrate shape of incident light flux arriving at an optical sensor part according to change in angles between major axis according to a structure illustrated in FIG. 19.

An optical wave guide (510) having multiple independent optical path in accordance with FIG. 19 has a light source installed at a second focal point (F2) of a first elliptical mirror (511) of three 3 dimensional elliptical mirrors (511, 512, 513) and optical sensors installed at second focal points (F2) of second and third elliptical mirrors (512, 513). In this case, optical path of incident light irradiating from a light source installed at a second focal point (F2) of a first elliptical mirror (511) to optical sensors installed at second focal points (F2) of second and third elliptical mirrors (512, 513) is as FIG. 19. Virtual reference lines (C21, C22, C23) connecting first focal points (F1) and second focal points (F2) of each three 3 dimensional elliptical mirrors (511, 512, 513) are realized to form constant angles ($\theta 21$, $\theta 22$, $\theta 22$).

As an example, an angle ($\theta 21$) formed by a reference line connecting a first focal point (F1) and a second focal point (F2) of a first elliptical mirror (511) and a reference line connecting a first focal point (F1) and a second focal point (F2) of a second elliptical mirror (512), and an angle ($\theta 22$) formed by a reference line connecting a first focal point (F1) and a second focal point (F2) of a first elliptical mirror (511) and a reference line connecting a first focal point (F1) and a second focal point (F2) of a third elliptical mirror (513) are formed to have same angles with each other.

As illustrated in FIG. 19, light irradiating from a light source installed at a second focal point (F2) of a first elliptical mirror (511) reflects once on an inside wall of a first elliptical mirror (511), and arrives at optical sensor parts placed at each second focal points after reflecting a second time on an inside wall of a second or a third elliptical mirror (512, 513). It shows that optical path is elongated by placing 3 dimensional elliptical mirrors (511, 512, 513), but reflection is minimized and thus a structure where condensed light arrives at an optical sensor part without loss of amount of light may be manufactured.

As illustrated in FIG. 19, an optical wave guide (510) having multiple independent optical path comprises, on side parts of two 3 dimensional mirrors (512, 513), a gas inlet (514), to which gas flows into, installed where spacial density of light emitting from a light source is low and a gas outlet (424) installed separated from the gas inlet (423), and gas inlet and gas outlet of the optical wave guide maintains sealing.

FIG. 20 illustrates results of simulation of energy of light per unit area arriving at optical sensor parts installed at second focal points (F2) of each second and third elliptical mirrors (512, 513) according to angles of main axis of second and third elliptical mirrors (512, 513) illustrated in FIG. 19, and it may be observed that as angles of main axis of second and third elliptical mirrors (512, 513) increase, maximum energy per unit area rapidly decreases.

FIG. 21 illustrates change in diameter of incident light flux arriving at optical sensor parts installed at second focal points (F2) of each second and third elliptical mirrors (512, 513) according to angles of main axis of second and third elliptical mirrors (512, 513) illustrated in FIG. 19, and it may be predicted that as angles of main axis of second and third elliptical mirrors (512, 513) increase, diameter of incident light from the center part of an optical sensor part increases.

When putting results of FIG. 20 and FIG. 21 together, it shows that increase in angles of main axis of second and third elliptical mirrors (512, 513) illustrated in FIG. 19 has an inefficient influence to optical energy and diameter of incident light flux, but there are advantages of being able to manufacture optimal optical sensors while minimizing influence of reflection.

FIG. 22A, FIG. 22B, FIG. 22C and FIG. 22D illustrate shape of incident light flux arriving at an optical sensor part according to change in angles between major axis according to a structure illustrated in FIG. 19. As in the result, it can be observed there are effects of light flux focusing to the center part of an optical sensor by modifying the angles between main axis of second and third elliptical mirrors (512, 513) illustrated in FIG. 19, it may be considered that measurements for gas with long wavelengths may be easily performed as energy per unit area increases by square of 1 or more compared to before being focused.

Figure 23:
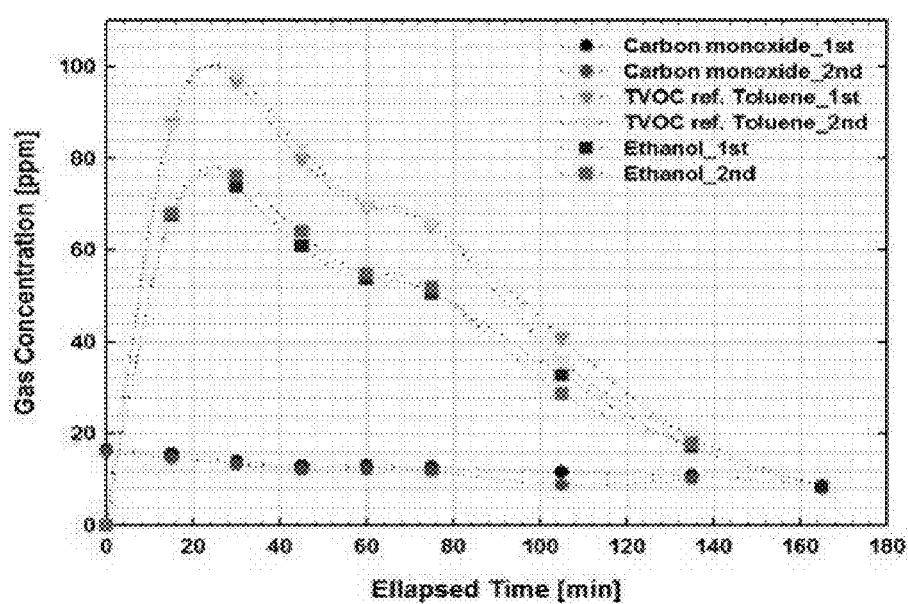
FIG. 23 illustrates results of analysis of gas emitted from a breath after drinking from multiple gas analyzing devices.

FIG. 23 illustrates results of analysis of gas emitted from a breath after drinking from a multi-gas analyzer (INNOVA 1312). Measurements show results of after time when drinking stops is set to 0, gas emitted through breath after a fixed time was collected and measured (expressed as $1^{st}$) immediately, and measured after a fixed time (drawing expressed as $2^{nd}$ is 1 hour 30 minutes to 2 hours), and are measurement results of concentration of carbon monoxide, TVOC, and alcohol. Carbon monoxide (infrared ray absorption wavelength: ~4.6 μm) emitted from breath shows a concentration of lower than about 20 ppm, but TVOCs (infrared ray absorption wavelength about 3.4 μm) and ethanol ((infrared ray absorption wavelength about 9.4 μm) shows concentration of about 80~100 ppm levels.

Figure 1:
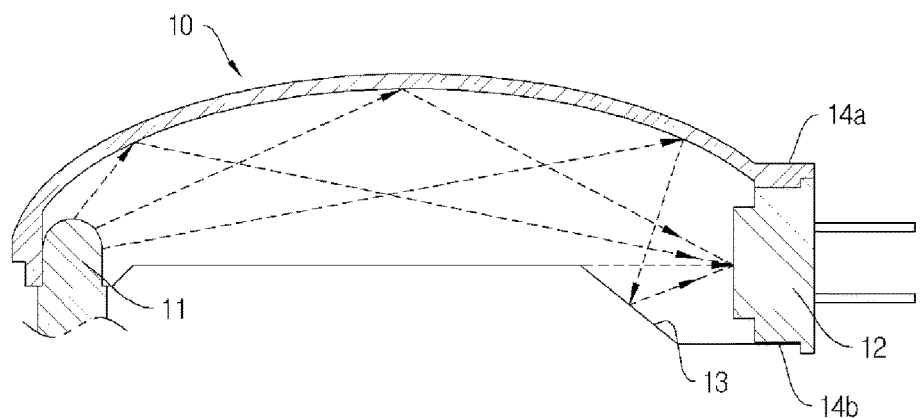
FIG. 1 to FIG. 7 illustrates prior gas sensors.
Figure 2:
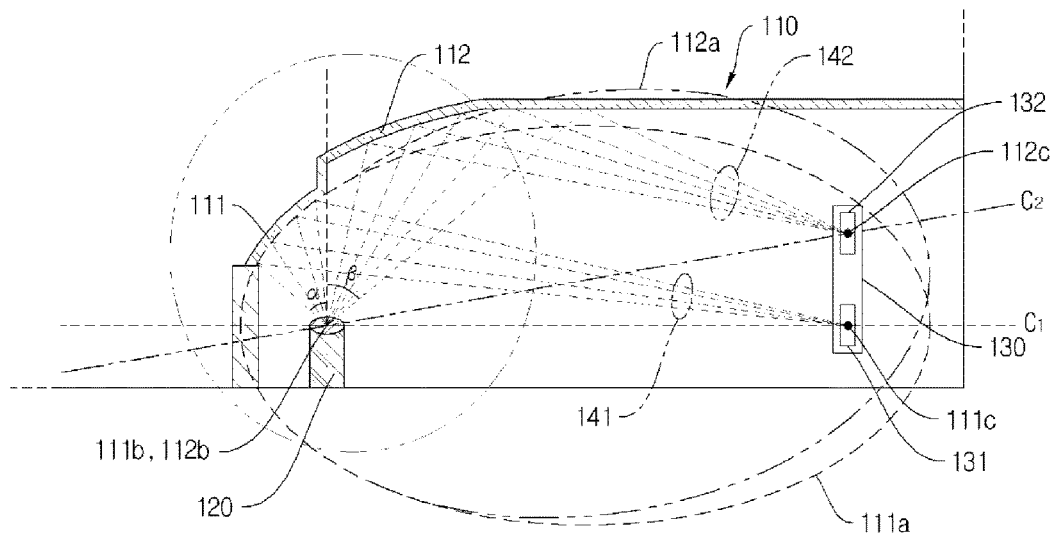
Figure 3:
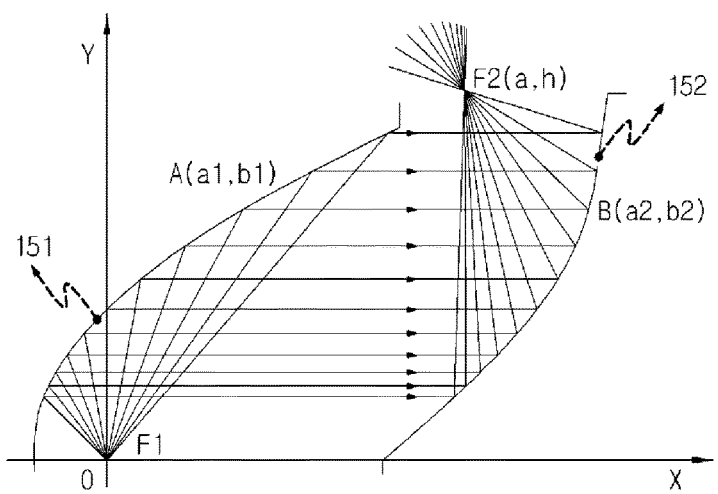
Figure 4:
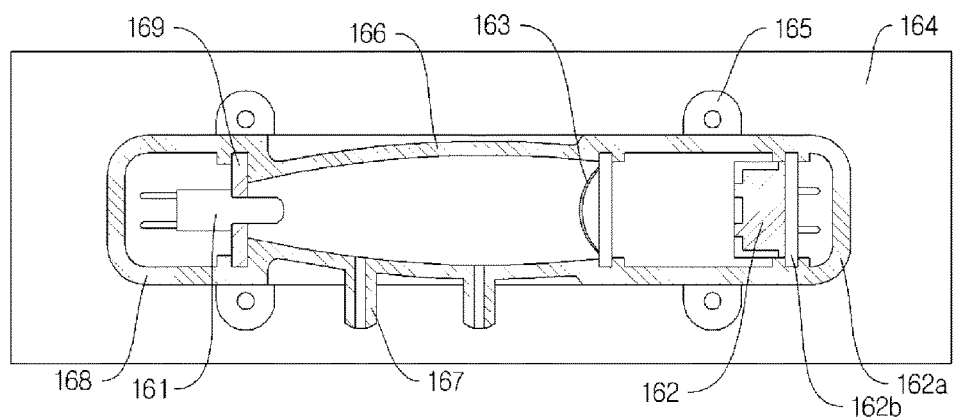
Figure 5:
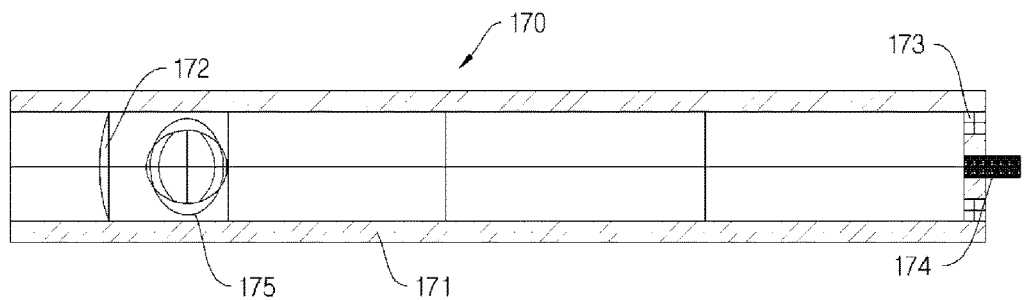
Figure 6:
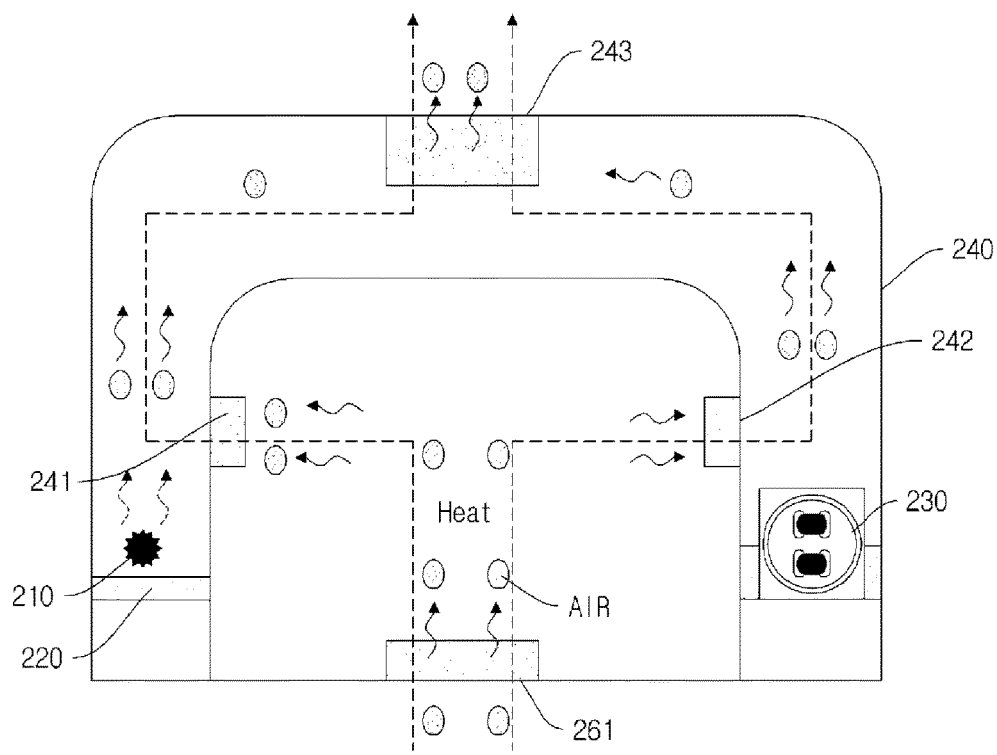
Figure 7:
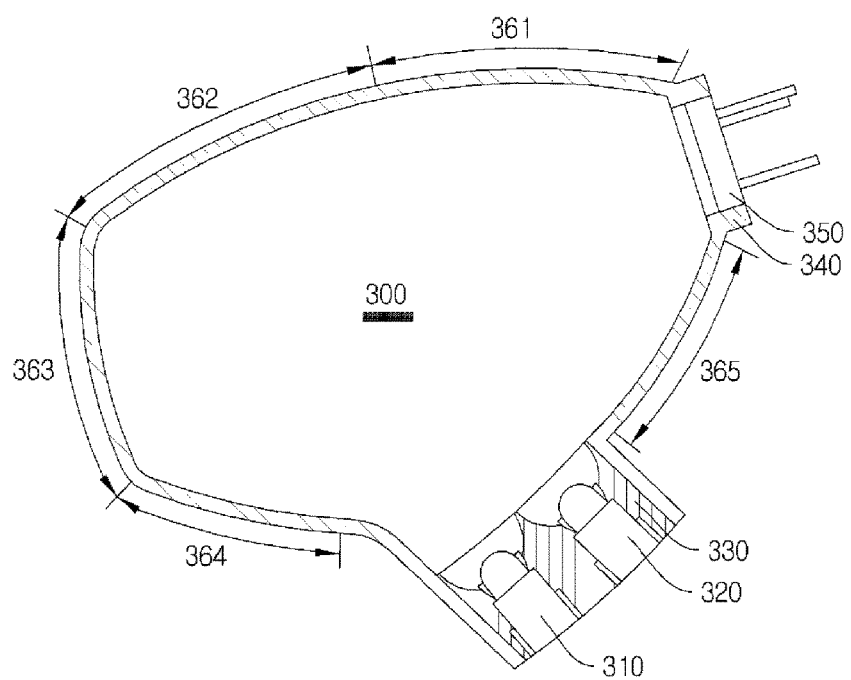
Figure 8:
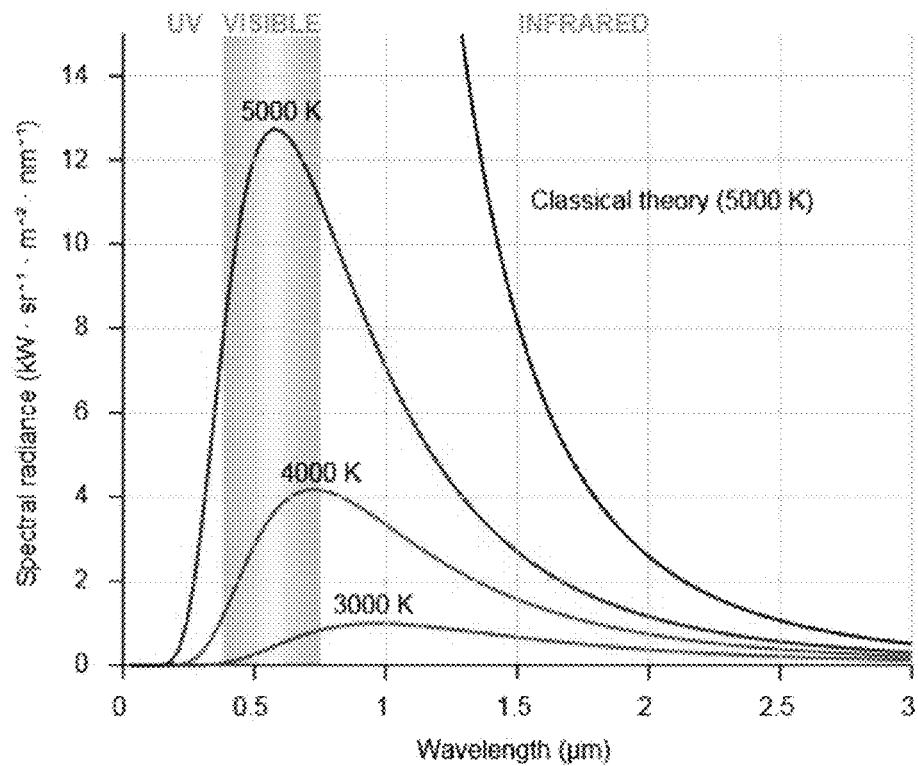
FIG. 8 illustrates the relationship between blackbody radiation and light intensity.

To Identify drunk driving results from concentration of ethanol emitting from the lungs when absorbed in the body, since a large amount of H—C compounds is emitted through breath after drinking, infrared sensor with long wavelengths (~9.4 μm) should be used for accurate concentration measurements. But, as illustrated in FIG. 8 and equation (1), since infrared rays irradiating from a light source have characteristics of light intensity decreasing as wavelength becomes longer, it is preferable to 1) use an infrared sensor with excellent sensing, or 2) choose a method for increasing energy per unit area by condensing infrared rays, and 3) select a structure that elongates the optical path as long as possible and increases efficiency of light by minimizing reflection inside the optical structure.

From the optical simulations provided above, 1) compared to patents provided in Korean Patent No. 10-0694635/10-0732708 and 10-1088360 and Korean Patent Laid-open Publication 2013-0058781, the structure of FIG. 10 and FIG. 14 has advantages of making optical path longer compared to registered of applied structures, 2) compared to Korean Patent No. 10-2008-0047896 and to Korean Patent No. 10-2009-0115590, since irradiating light may be effectively condensed without using a separate condenser and irradiate to an optical sensor part, there are advantages of having no factors of cost increase.

3) compared to Korean Patent No. 10-2008-0016685 and to Korean Patent No. 10-2009-0068892, a reference sensor may be equipped at a first optical sensor part, and by installing a sensor measuring gas, which is a target for measurement, at a second optical sensor part of a structure with a form of structure in FIG. 14, reliability may be improved.

That is, as an example, when intending to manufacture an optical gas sensor for measuring drinking, if a carbon monoxide sensor with a wavelength absorption of 4.6 μm is placed at a first optical sensor part, and an ethanol sensor with a wavelength absorption of 4.6 μm is placed at a second optical sensor part and light source is illuminated, relatively large amount of energy absorption is possible during initial operation of the sensor, and selection in respect to other gas is excellent, and considering that there are almost no carbon monoxide in the atmosphere, output status of light source based on sensor output is checked, and by comparative evaluation of output of ethanol sensor applying this, sensitivity change of sensor according to secular change of light source is compensated, and thus may equip characteristics of securing long-term reliability.

Therefore, manufacturing sensor with all of the characteristics of an infrared optical gas sensor mentioned individually in the described registered and applied patents, and raised up in the beginning of the present invention, in which 1) a structure that may actively deal with secular change of an infrared ray light source, 2) a high performance sensor or structure that may improve light intensity, 3) a structure with a long optical path, and a structure that minimizes reflections inside, 4) irradiating in a field of view of an optical sensor part by incident light arriving at an optical sensor part is focused to a small radius at the center of an optical sensor is possible.

Also, by installing gas inlet (a structure that pushes in gas to measure ethanol or optical structure used for measuring gas by suctioning outside air using a small pump) and an outlet in areas with low spatial density of infrared rays, manufacturing an optical sensor without decrease in optical efficiency is possible.

Although exemplary embodiments have been described herein, it should be understood by those skilled in the art that these embodiments are given by way of illustration only, and that various modifications, variations and alterations can be made without departing from the spirit and scope of the invention. The scope of the present invention should be defined by the appended claims and equivalents thereof.

What is claimed is:

1. An optical gas sensor comprising:
an optical wave guide including
a first elliptical mirror formed along at least part of a first 3-dimensional ellipsoid and having a first focal point and a second focal point,
a second elliptical mirror formed along at least part of a second 3-dimensional ellipsoid and having the first focal point and a third focal point, and
a third elliptical mirror formed along at least part of a third 3-dimensional ellipsoid and having the first focal point and a fourth focal point,
wherein a first angle between a first virtual reference line connecting the first focal point and the second focal point and a second virtual reference line connecting the first focal point and the third focal point is equal to a second angle between the first virtual reference line and a third virtual reference line connecting the first focal point and the fourth focal point;
a first optical sensor installed at one of the first, second, third, and fourth focal points; and
a first light source installed at the first, second, third, or fourth focal points where the first optical sensor is not installed,
wherein
the first focal point is a common focal point for the first, second, and third 3-dimensional ellipsoids, and
light within the optical wave guide, which is emitted from the first light source, pass through or reach the first focal point during propagation from the first light source to the first optical sensor.

2. An optical gas sensor according to claim 1, further comprising:
a second light source; and
a third light source,
wherein
the first optical sensor is installed at the first focal point;
the first, second and third light sources are installed at the second, third, and fourth focal points, respectively; and
a third angle between the second virtual reference line and the third virtual reference line is selected from a range of 20~60 degrees.

3. An optical gas sensor according to claim 1, further comprising:
a second optical sensor installed at the fourth focal point, wherein
the first optical sensor is installed at the second focal point;
the first light source is installed at the third focal point; and
a third angle between the second virtual reference line and the third virtual reference line is selected from a range of 20~60 degrees.

4. An optical gas sensor according to claim 1, further comprising:
a second light source,
wherein
the first optical sensor is installed at the second focal point;
the first and second light sources are installed at the third and fourth focal points, respectively; and
a third angle between the second virtual reference line and the third virtual reference line is selected from a range of 10~180 degrees.

5. An optical gas sensor according to claim 1, further comprising:
a second optical sensor installed at the fourth focal point, wherein
the first optical sensor is installed at the third focal point;
the first light source is installed at the second focal point; and
a third angle between the second virtual reference line and the third virtual reference line is selected from a range of 20~60 degrees.

6. An optical gas sensor according to claim 1, further comprising:
a second optical sensor installed at the third focal point; and
a third optical sensor installed at the fourth focal point, wherein
the first optical sensor is installed at the second focal point; and
the first light source is installed at the first focal point.

7. An optical gas sensor according to claim 1, wherein a third angle between the second virtual reference line and the third virtual reference line is selected from a range of 20~60 degrees.

* * * * *